(12) United States Patent
Yang et al.

(10) Patent No.: US 9,989,601 B2
(45) Date of Patent: Jun. 5, 2018

(54) RECONFIGURABLE MRI-GUIDED SURGICAL APPARATUS

(71) Applicant: Quality Electrodynamics, LLC, Mayfield Village, OH (US)

(72) Inventors: Xiaoyu Yang, Indiana, PA (US); Tsinghua Zheng, Aurora, OH (US); Shinya Handa, Mayfield Village, OH (US)

(73) Assignee: Quality Electrodynamics, LLC, Mayfield Village, OH (US)

( * ) Notice: Subject to any disclaimer, the term of this patent is extended or adjusted under 35 U.S.C. 154(b) by 931 days.

(21) Appl. No.: 14/484,399

(22) Filed: Sep. 12, 2014

(65) Prior Publication Data

US 2015/0168509 A1  Jun. 18, 2015

Related U.S. Application Data

(60) Provisional application No. 61/917,424, filed on Dec. 18, 2013.

(51) Int. Cl.
*A61B 5/00* (2006.01)
*G01R 33/34* (2006.01)
*A61B 10/02* (2006.01)
*A61B 5/055* (2006.01)
(Continued)

(52) U.S. Cl.
CPC ...... *G01R 33/34084* (2013.01); *A61B 5/0555* (2013.01); *A61B 5/708* (2013.01); *A61B 10/0233* (2013.01); *A61B 90/11* (2016.02); *A61B 90/17* (2016.02); *A61B 5/0037* (2013.01); *A61B 2010/0208* (2013.01)

(58) Field of Classification Search
CPC ....... A61B 90/11; A61B 90/17; A61B 5/0555; A61B 5/708; A61B 10/0233; A61B 5/0037; A61B 2010/0208; G01R 33/34084
See application file for complete search history.

(56) References Cited

U.S. PATENT DOCUMENTS 9,014,784 B2 * 4/2015 Yang ................ A61B 90/17
                                               5/601
2009/0054757 A1 * 2/2009 Noras ............... A61B 6/0414
                                               600/415
(Continued)

*Primary Examiner* — Joel Lamprecht
(74) *Attorney, Agent, or Firm* — Eschweiler & Potashnik, LLC

(57) ABSTRACT

Apparatus associated with improved magnetic resonance imaging (MRI) guided needle biopsy procedures (e.g., breast needle biopsy) are described. One example apparatus includes a support structure configured to support a patient in a face-down prone position where a breast of the patient is positioned in a first free hanging pre-imaging position. The example apparatus includes an immobilization structure configured to reposition the breast into an immobilized position suitable for MRI and for medical instrument access. The immobilization structure may include a removable biopsy plate, a removable side coil, a pressure plate, and MRI coils. The MRI coils are configured to be repositioned from a first position associated with the free hanging pre-imaging position to a second position associated with the immobilized position to facilitate improving the signal to noise ratio associated with signal received from the breast through the MRI coils.

19 Claims, 29 Drawing Sheets

(51) Int. Cl.
   *A61B 90/17*   (2016.01)
   *A61B 90/11*   (2016.01)

(56) References Cited

U.S. PATENT DOCUMENTS

2014/0128723 A1* 5/2014 Yang ..................... A61B 90/17
                                                        600/415
2014/0213886 A1* 7/2014 Menon ............... A61B 10/0275
                                                        600/411

* cited by examiner

Front View

RECONFIGURABLE MRI-GUIDED SURGICAL APPARATUS

CROSS REFERENCE TO RELATED APPLICATIONS

This application claims the benefit of U.S. Provisional Application 61/917,424 filed Dec. 18, 2013.

BACKGROUND

Many patents have issued on breast specific coils for magnetic resonance imaging (MRI). See, for example, U.S. Pat. Nos. 7,084,631 and 7,970,452. Some of these breast specific coils are designed to improve imaging by increasing signal-to-noise ratio (SNR) by adding coils or by facilitating repositioning coils. Some of these breast specific coils are suitable for MRI-guided surgical procedures.

Conventional breast specific coils may include plates that can be moved to immobilize a breast and some even include coils that can be added or removed. Some conventional breast specific coils include center supports that may include RF coils for bilateral imaging. While these conventional breast specific coils have improved breast imaging and have improved MRI-guided procedures, further improvements are still sought.

MRI detects the nuclear magnetic resonance (NMR) signals produced by protons in the presence of a strong magnetic field after specific excitation by radio frequency (RF) energy. The NMR signals are detected by antennae known as "coils." In different usages, the term "coil" may refer to just the antenna, or may refer to the antenna, its housing, and support structure. The term "coil" may refer to an assembly that includes two or more coils. An operable part of the coil may be referred to as a "coil element." The operable part may also be referred to as the coil.

MRI involves sampling in k-space to acquire an NMR signal from an object exposed to magnetic fields, gradients, and RF energy produced by an MRI apparatus. The quality of a magnetic resonance image may depend, at least in part, on the proximity of the apparatus (e.g., coils) producing the fields, gradients, and RF energy to which the object being imaged is subjected. The quality may also depend on the number, proximity, and orientation of coils receiving NMR signals from an object. MRI is frequently used for diagnostic medical imaging. Recently, MRI has also been used to guide surgical techniques. For example, MRI has been used to guide needle biopsies.

The quality of the NMR signal received from an object being imaged may be described, at least in part, by its SNR. One goal in an MRI session is to have a good (e.g., high) SNR. SNR is a function of several factors. One of the factors includes how close a coil is located to the object being imaged. Theoretically, a separate individual coil could be fashioned for each MRI session to account for differences between patients. Practically, this is unlikely due to both time and cost constraints. Therefore, one-size-fits-all coils are generally employed, or a very small set of different sized coils (e.g., adult, child) may be employed. Unfortunately, one-size-fits-all coils generally yield poor (e.g., low) SNR. Additionally, the need to accommodate access to a breast for an interventional device, such as a biopsy needle, during breast MRI may also produce a competition between proximity for high SNR and spacing to allow access.

Breast MRI has become increasingly important over time. Thus, numerous patents have been issued in this space. For example, U.S. Pat. No. 7,084,631 describes an MRI array coil system for breast imaging. The coil system includes top and bottom openings for receiving and supporting breasts, and side windows for accessing the breasts from the side while the patient is positioned on the apparatus.

U.S. Pat. No. 7,970,452 describes an open architecture imaging apparatus and coil system for MRI. The '452 patent describes an apparatus where RF coils and compression plates can be positioned, repositioned, held in place, and otherwise manipulated to provide improved SNR and an improved patient experience. The '452 patent describes a separable and reconfigurable coil system that may be optimized for particular imaging purposes including, but not limited to, bilateral imaging, unilateral imaging, imaging of the chest wall for mastectomy patients, and interventional procedures. The '452 patent recites that "a fundamental aspect to this disclosure of technology is the separation of patient support structures from RF coil system." (Column 7, lines 18-20). The '452 patent also recites how "the ability to accept modular coil elements in an interchangeable support structure is a unique aspect of the present invention." (Column 10, lines 64-66). Thus, some patents have described modular coil elements that can be added or removed from a larger patient support structure.

Some conventional apparatus exist that employ the one-size-fits-all approach for supporting needle biopsies for acquiring breast tissue. The one-size-fits-all approach to coil design for breast imaging may lead to sub-optimal results. Conventional apparatus may include a one-size-fits-all coil and a one-size-fits-all biopsy plate.

FIG. 1a illustrates a front view of a coil 100. FIG. 1b illustrates a side view of coil 100. Coil 100 includes a housing 110 and an operational part 120. The operational part 120 may include copper wire or traces and attached circuitry. The wire and the circuitry may operate as a transceiver that can both transmit RF energy into an object to be imaged and receive NMR signals resulting from the application of that RF energy. How close the copper wire can be placed to an object to be imaged is a function of at least the thickness T1 of the housing 110. Conventionally, coil 100 has been a monolithic item that can be positioned or manipulated as a single item.

FIG. 2a illustrates a front view of a biopsy plate 200. FIG. 2b illustrates a side view of biopsy plate 200. FIG. 2c illustrates a front view of another biopsy plate 220. Biopsy plate 200 is illustrated being divided into sixteen regions. These regions may be fashioned by internal dividers. Biopsy plate 200 may be made, for example, from plastic. During a surgical procedure (e.g., biopsy), biopsy plate 200 is likely going to come in contact with biological fluids, including blood. Therefore a separate biopsy plate 200 will likely be employed for each biopsy and the biopsy plate 200 will likely be cleaned and sterilized or discarded after use.

The sixteen regions may measure, for example, one inch by one inch, two centimeters by two centimeters, or other dimensions. A needle biopsy may need greater precision for positioning a needle than can be provided by a one inch by one inch opening. Therefore, a needle positioning block 210 may be positioned in one of the sixteen regions. The needle positioning block 210 is also illustrated with sixteen regions. While sixteen regions are illustrated in both biopsy plate 200 and needle positioning block 210, different numbers of regions may be found in different biopsy plates and in different needle positioning apparatus. In second biopsy plate 220, one of the regions houses the needle positioning block 210. In a needle biopsy, the needle would be inserted to a desired depth into a volume (e.g., breast) after a location within the volume was identified during imaging. The position and direction of travel of the needle is controlled by the region in the needle positioning block 210 through which the needle is inserted. Both the biopsy plate 200 and the needle positioning block 210 are likely to be cleaned and sterilized or discarded after a procedure.

FIG. 3 illustrates a side view of a coil 300 paired with a biopsy plate 310. Coil 300 includes an operational part 301 and a housing 302. The biopsy plate 310 is illustrated with a needle positioning block 311 housed in one of the regions in biopsy plate 310. During the image acquisition portion of an MRI-guided needle biopsy, the coil 300 and the biopsy plate 310 may be positioned close together and as close to a breast as possible. How close the coil 300 can be placed to the volume to be imaged depends on the thickness T3 of the housing of the coil 300 and the thickness T4 of the biopsy plate 310. In one embodiment, when the imaging portion of the MRI-guided needle biopsy is complete, the coil 300 may be removed to provide access to the biopsy plate 310 and then the needle positioning block 311 may be inserted into the biopsy plate 310 at a relevant location. In one embodiment, during a first imaging portion of a biopsy procedure, the side coil 300 may be in position and the biopsy plate 310 may not be in position. For example, the side coil 300 may be mounted in the apparatus while the biopsy plate 310 is not mounted in the apparatus. After the first imaging portion, the side coil 300 may be removed from the apparatus and replaced with the biopsy plate 310.

A biopsy plate is likely to come in contact with biological fluid during a biopsy. Therefore, it is likely that the biopsy plate will need to be destroyed or at least rigorously cleaned or sanitized after use. Coils are expensive. Coils are also generally housed in a solid housing. Therefore, it is unlikely that a needle will be pushed through a coil, both because it would damage the coil and because it would be undesirable to have the coil come in contact with the biological fluid. Therefore, during an MRI-guided biopsy, the coil may first be positioned beside the biopsy plate to facilitate acquiring an image and registering the image to the biopsy plate. After the image is acquired, the coil may be removed so that the needle can be pushed through the biopsy plate. Positioning the coil and then removing the coil requires skilled operator attention, and thus takes time. Also, as described above, the distance between the coil and the volume to be imaged affects the SNR for signal acquired from the object being imaged. In general, having the coil closer to the volume during an MRI procedure improves SNR while having the coil farther from the volume negatively impacts SNR.

SNR may also depend on the number of coils and the orientation of the coils used to image a volume. The anatomy of a volume to be imaged may control both the number of coils that can be used and the proximity of those coils. For example, it is possible to surround a knee with a number of coils and to bring those coils into very close proximity with the knee. However, for an image guided needle biopsy of a breast, it may not be possible to surround the volume and it may not be possible to bring the coils as close to the volume as desired due to the requirement of fixing the volume with the biopsy plate.

FIG. 4a illustrates a view looking towards the feet from the head of a patient of portions of an apparatus 405. FIG. 4b illustrates a top view of apparatus 405. Apparatus 405 may support a patient who is lying face down during an MRI-guided needle biopsy. Apparatus 405 includes housing 410, a biopsy plate 420, and a central fixed element 430. Apparatus 405 includes an opening 499 through which breast 400 may hang. Apparatus 405 may have two such openings. In one embodiment, the central fixed element 430 may not be present.

FIG. 4a also represents a breast 400 as it might appear when viewed from the head of a patient that is lying face down on apparatus 405. Initially, the breast 400 would hang down through opening 499 in the apparatus 405. In the initial positioning, breast 400 might be able to move, making it difficult, if even possible at all, to accurately place a needle into a region of interest identified during an MRI-guided biopsy. Therefore, before imaging, the breast 400 may be compressed into a different shape by being squeezed between biopsy plate 420 and another fixed element 430. In one embodiment, the biopsy plate 420 may be replaced with a side coil and the breast may be squeezed between a side coil and another fixed element 430. After imaging, the side coil may be replaced with the biopsy plate 420. In one embodiment, the biopsy plate 420 may squeeze the breast in the same directions and with the same forces as the side coil did.

FIG. 5a illustrates a view looking towards the feet from the head of a patient of portions of an apparatus 505. FIG. 5b provides a top view of apparatus 505. Apparatus 505 may support a patient who is lying face down using support structure 510. Apparatus 505 includes a biopsy plate 520 and a central fixed element 530. Apparatus 505 includes an opening 599 through which breast 500 may hang. Apparatus 505 may have two such openings.

FIG. 5a also represents breast 500 as it might appear when viewed from the head of a patient that is lying face down on apparatus 505. The breast 500 is illustrated after it has been compressed between biopsy plate 520 and fixed element 530. A coil 540 is illustrated beside biopsy plate 520. The breast 500 may be imaged using coil 540. Other coils may also be involved in imaging breast 500. Note that as biopsy plate 520 compresses breast 500, breast 500 is moved farther from coil 540. With the breast 500 compressed into a shape that can be maintained during imaging and then during needle insertion, the imaging may proceed. In one embodiment, a two-step process may be performed. First, the breast may be compressed and imaged. Second, the side coil may be removed to provide access to the biopsy plate.

FIG. 6 illustrates breast 500 as it might appear when viewed from the head of a patient that is lying face down on apparatus 505. The breast 500 is illustrated after a region of interest 550 has been identified. A needle 560 may be inserted through the biopsy plate 520 to acquire tissue from the region of interest 550. A needle positioning block may be positioned in the biopsy plate 520 before the needle 560 is inserted to facilitate more accurate placement of the needle 560. The coil 540 may be removed before the needle 560 is inserted into the region of interest 550.

BRIEF DESCRIPTION OF THE DRAWINGS

The accompanying drawings, which are incorporated in and constitute a part of the specification, illustrate various example systems, apparatus, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be

DETAILED DESCRIPTION

Figure 1A:
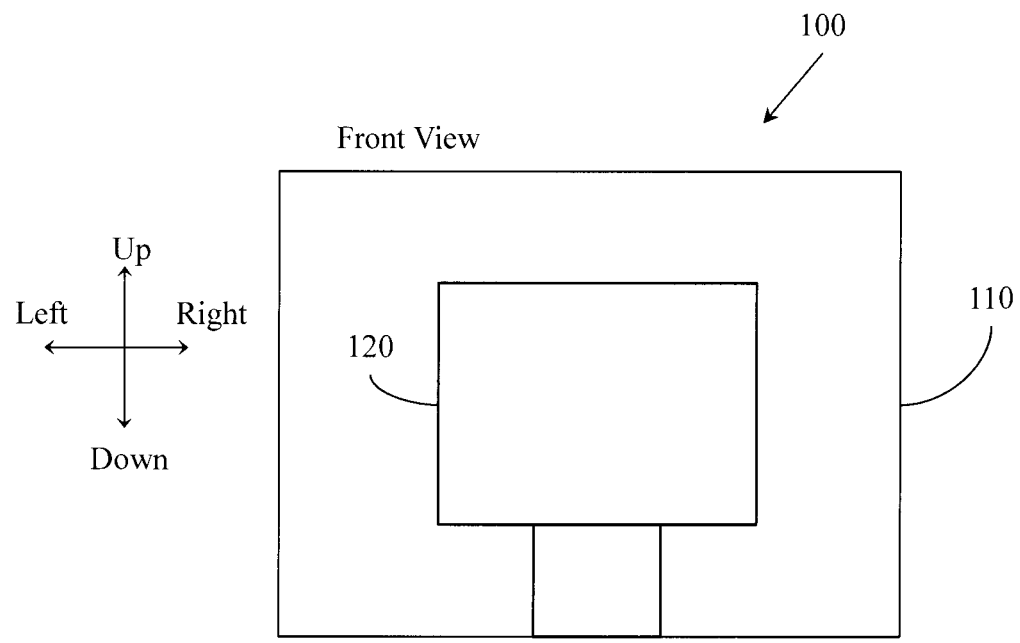
FIGS. 1a and 1b illustrate an MRI coil.
Figure 1B:
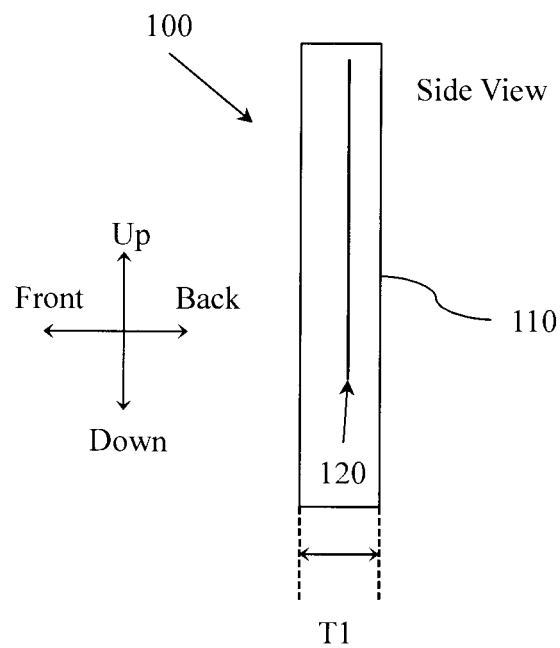
Figure 2B:
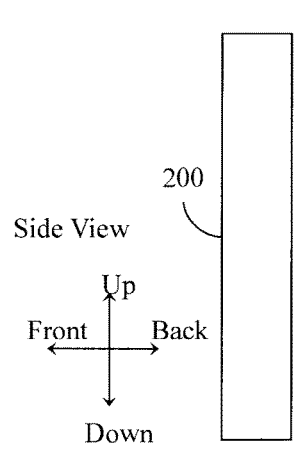
FIGS. 2a, 2b, and 2c illustrate a biopsy plate.
Figure 2A:
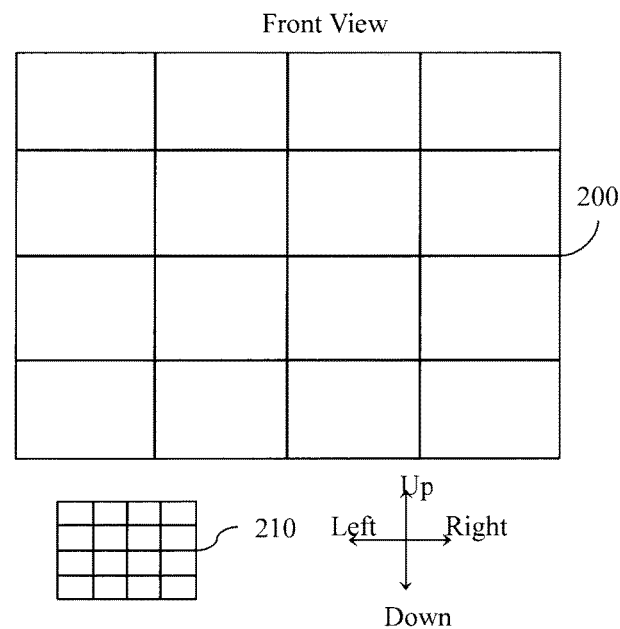
Figure 2C:
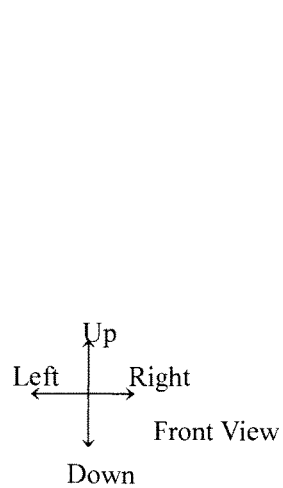
Figure 3:
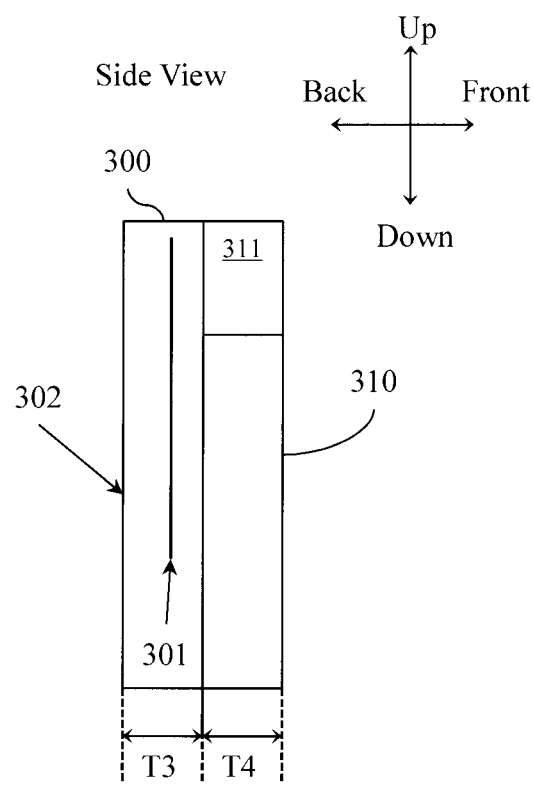
FIG. 3 illustrates an MRI coil paired with a biopsy plate.
Figure 4A:
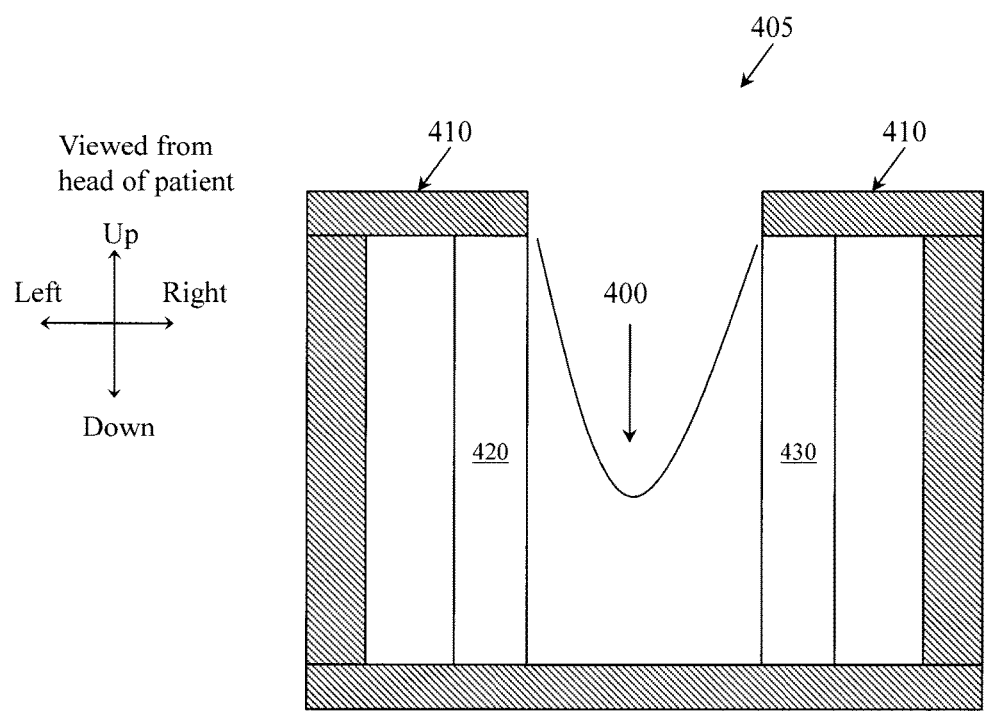
FIGS. 4a and 4b illustrate a portion of an MRI-guided surgical apparatus.
Figure 4B:
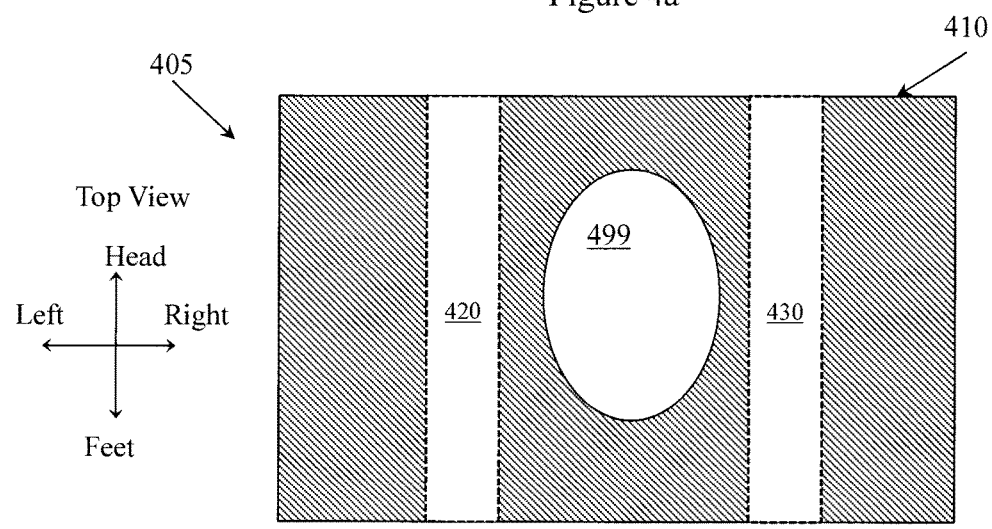
Figure 5A:
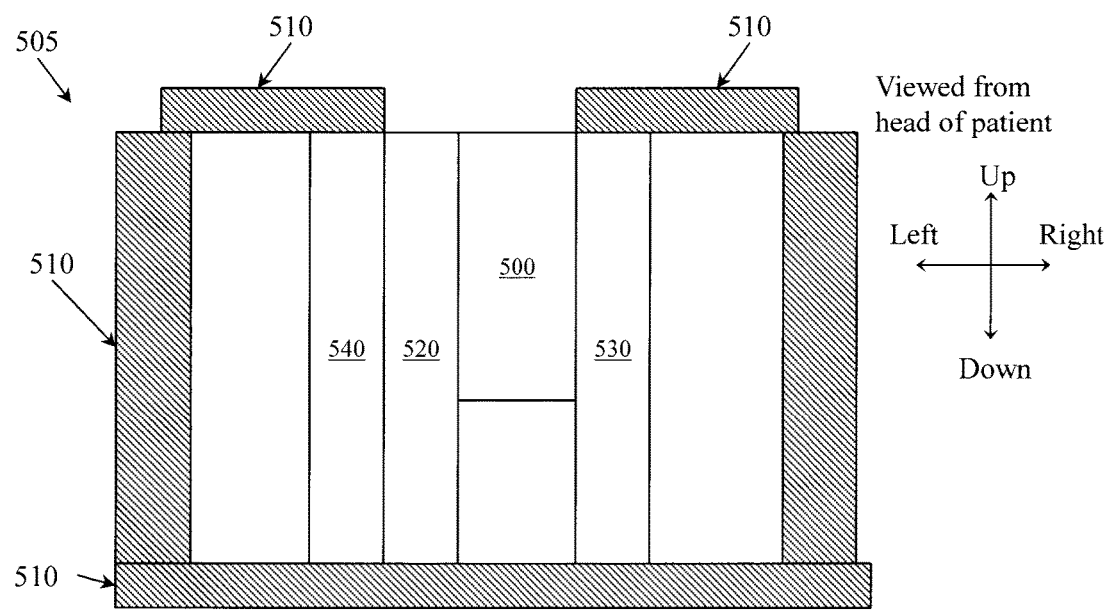
FIGS. 5a and 5b illustrate a portion of an MRI-guided surgical apparatus.
Figure 5B:
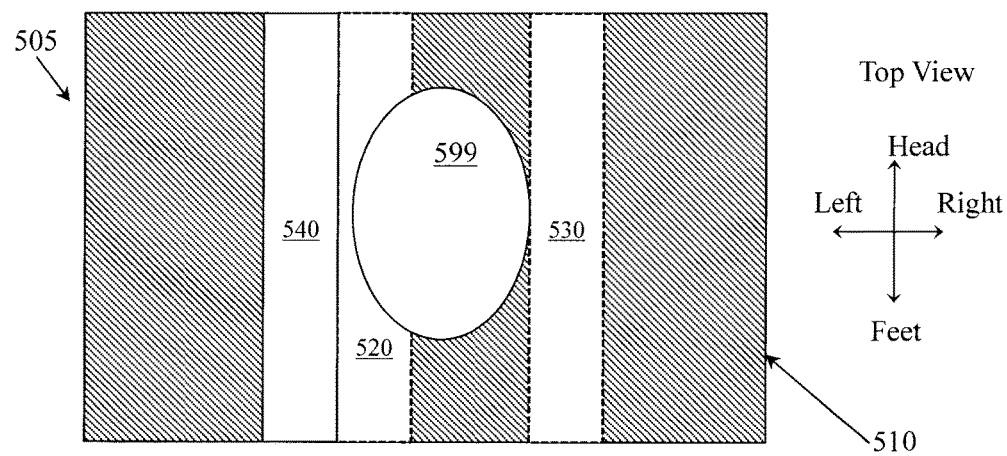
Figure 6:
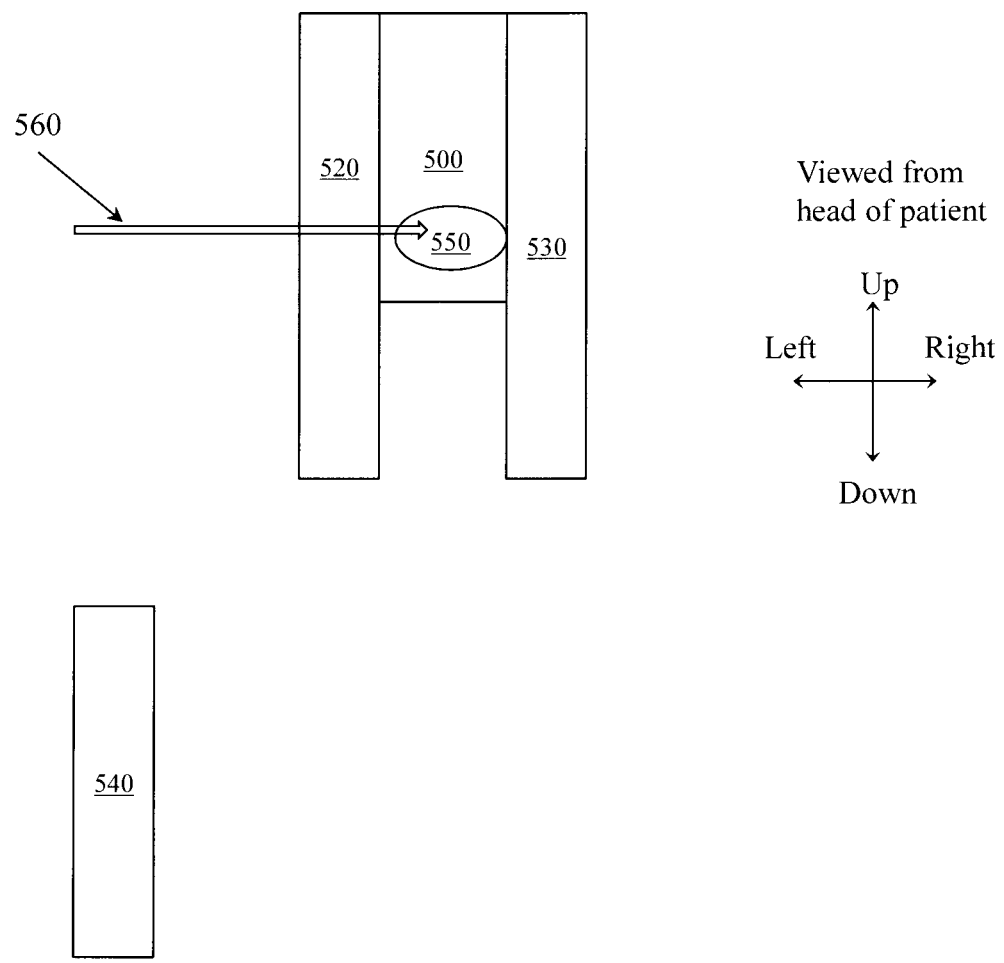
FIG. 6 illustrates a portion of an MRI-guided surgical apparatus.

Example apparatus described herein concern a reconfigurable MRI-guided surgical apparatus for supporting MRI-guided surgical procedures. Example apparatus provide additional coils, provide coils that may be repositioned to facilitate placing a coil closer to a volume to be imaged, provide attachments that facilitate reconfiguration by moving coils out of the way (e.g., removing coils), provide a center coil that can be rotated from a bilateral imaging mode to a unilateral high resolution imaging mode, or facilitate reducing operator actions required to reposition (e.g., remove) a coil to gain access to a medical instrument guidance assembly.

Example apparatus accept a modular medical instrument guidance assembly that may be inserted, used, and then removed from a larger supporting apparatus. One example surgical procedure is a needle biopsy and thus one example medical instrument guidance assembly is a biopsy plate. A pillar and post apparatus may also be employed to hold and position a needle or other surgical instrument. In one embodiment, the pillar and post assembly may be a portion of a robotic apparatus or may be computer controlled. Other surgical procedures may include, but are not limited to, a trans-cannula procedure, cryoablation, laser ablation, hyperthermia, medicament delivery, percutaneous removal of a lesion, cyst, or other item, and percutaneous draining of a lesion, cyst, or other item.

Example apparatus include an inner assembly that may be housed, placed in, or otherwise associated with a larger breast coil apparatus or breast supporting apparatus. An example inner assembly may have one or more guides and one or more attachment points for biopsy plates that facilitate making the biopsy plates movable and/or lockable. An example inner assembly may also have one or more guides, and one or more attachment points for side coils that facilitate making the side coils movable, lockable, and/or removable. An example inner assembly may also have one or more rails or attachment points for a pillar and post assembly. The pillar and post assembly may be computer controlled. An example inner assembly may also have one or more guides, attachment points, and hinges for a center assembly that facilitate making the center assembly movable, lockable, and/or able to be rotated from positions including a horizontal orientation to a vertical orientation. An example inner assembly facilitates moving biopsy plates towards and away from a breast to facilitate immobilizing a breast to be imaged. An example inner assembly also facilitates moving side coils towards and away from the breast to bring the side coils to a desired proximity for imaging the breast. Since side coils may partially block access to a biopsy plate, an example inner assembly may also facilitate repositioning side coils (e.g., removing) from the inner volume assembly. Repositioning or removing a side coil may provide access to a biopsy plate, pillar and post assembly, or other medical instrument guidance assembly. Removing a side coil may also allow a biopsy plate, pillar and post assembly, or other medical instrument guidance assembly to be inserted into the assembly where the side coil had previously been positioned. An example inner assembly may also facilitate rotating a center coil from an upright position used for bilateral imaging to a horizontal position used for unilateral imaging. Being able to rotate a center coil to a position beneath a breast may increase the number of coils available for imaging and may also facilitate quadrature imaging by orienting the center coil perpendicular to a side coil. In quadrature imaging reception, NMR signals are detected in two orthogonal directions by two independent coils that cover the same volume of interest. In one embodiment, the center coil may also be rotated away from the breast or imaged area. Rotating the center coil away from the imaging area may reduce coupling.

Figure 28:
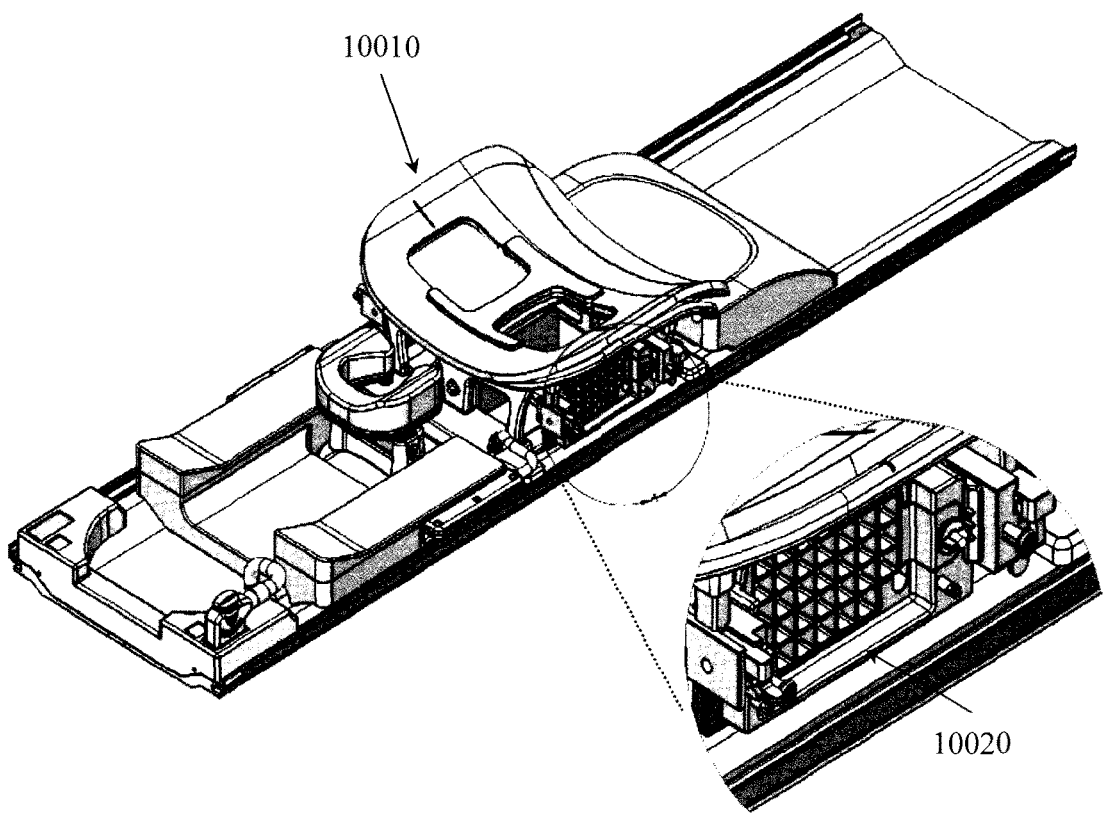
FIG. 28 illustrates a portion of an example reconfigurable MRI-guided surgical apparatus with the biopsy plate mounted and the side coil not mounted.

FIG. 28 illustrates a biopsy plate 10020. FIG. 28 illustrates how the biopsy plate 10020 is used in a biopsy procedure. In the procedure, the side coil is removed from the guide assembly 10010 and stored in, for example, the pocket of a hand rest. The biopsy plate 10020 or biopsy grid in its mounting adaptor can be mounted in or on and then removed from the guide assembly. In one embodiment, the biopsy plate 10020 or biopsy grid may be snapped into the larger support assembly 10010. The operator may still perform MRI imaging in the illustrated configuration without using the side coil. The SNR is not as good as can be achieved with the side coil in place but is acceptable for biopsy purposes. This approach is superior to conventional approaches for at least two reasons. The first is that it is easier for an operator to perform the biopsy with the biopsy plate 10020 snapped in place and the side coil removed. The second is for future upgrades. As new side coils are designed and manufactured, they can be used with the apparatus 10010 by simply being mounted and unmounted, which does not require creating an entirely new apparatus to accommodate advances in coils.

Figure 27:
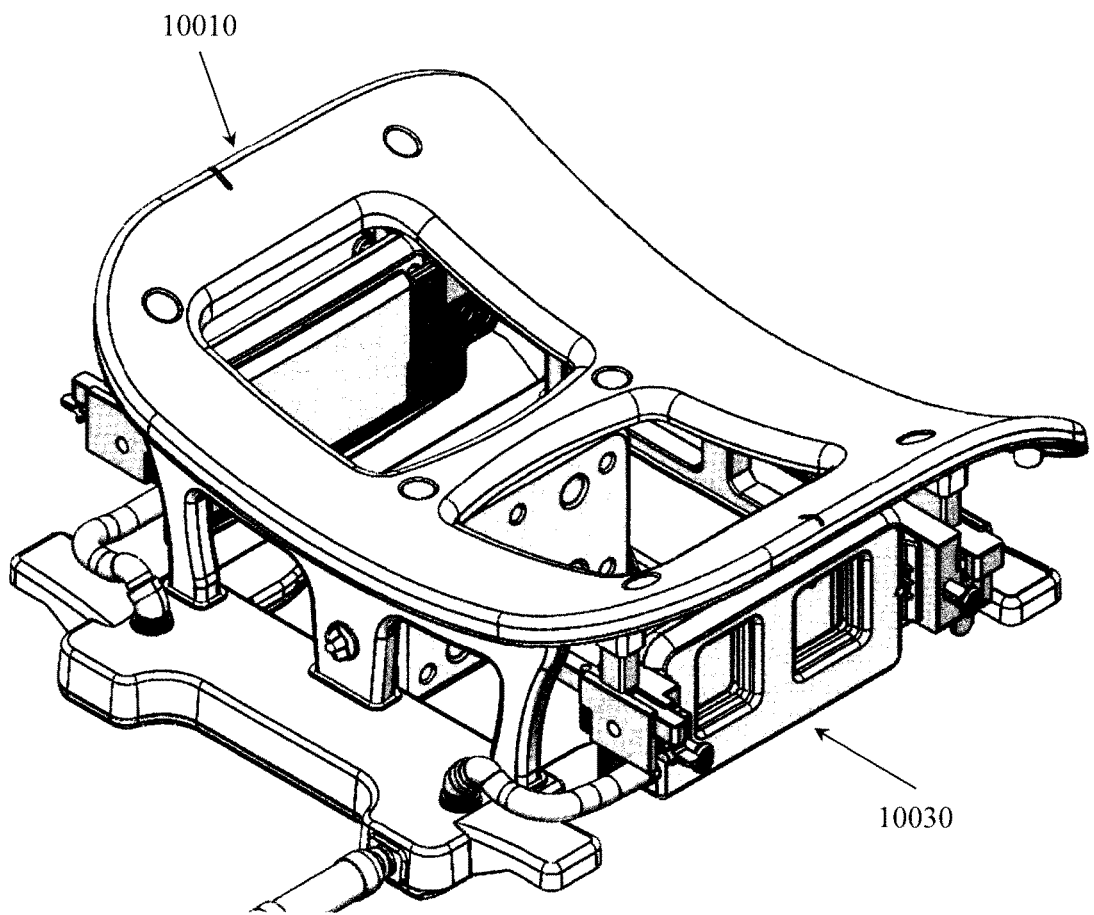
FIG. 27 illustrates a portion of an example reconfigurable MRI-guided surgical apparatus with the side coil mounted and the biopsy plate removed.

FIG. 27 illustrates the supporting apparatus 10010 in an imaging-only mode with the side coil 10030 in place. This imaging-only mode may require high SNR and may be used first, before a biopsy is performed, to acquire high SNR images. The high SNR images may first be used to make a diagnosis. The high SNR images may then be used to plan a later biopsy or to facilitate configuring the biopsy plate 10020 or biopsy grid that will facilitate guiding the biopsy. A patient will lay face down on the apparatus 10010. The patient's abdomen will be supported by the support pad. The patient's head is supported by the head rest. The patient's arm and hand are supported by the hand rest if the hand and arm are in the raised position. The side coil 10030 is mounted (e.g., snap mounted) in the guide assembly and is used to get high SNR images. After the high SNR images are acquired, the side coil 10030 may be removed and replaced with the biopsy plate 10020 as illustrated in FIG. 28. In one embodiment, the biopsy plate 10020 may already have been in place and thus removing the side coil 10030 provides access to the biopsy plate 10020. In one embodiment, when a biopsy procedure is to be performed, the side coil 10030 may not be employed during the procedure.

Figure 29:
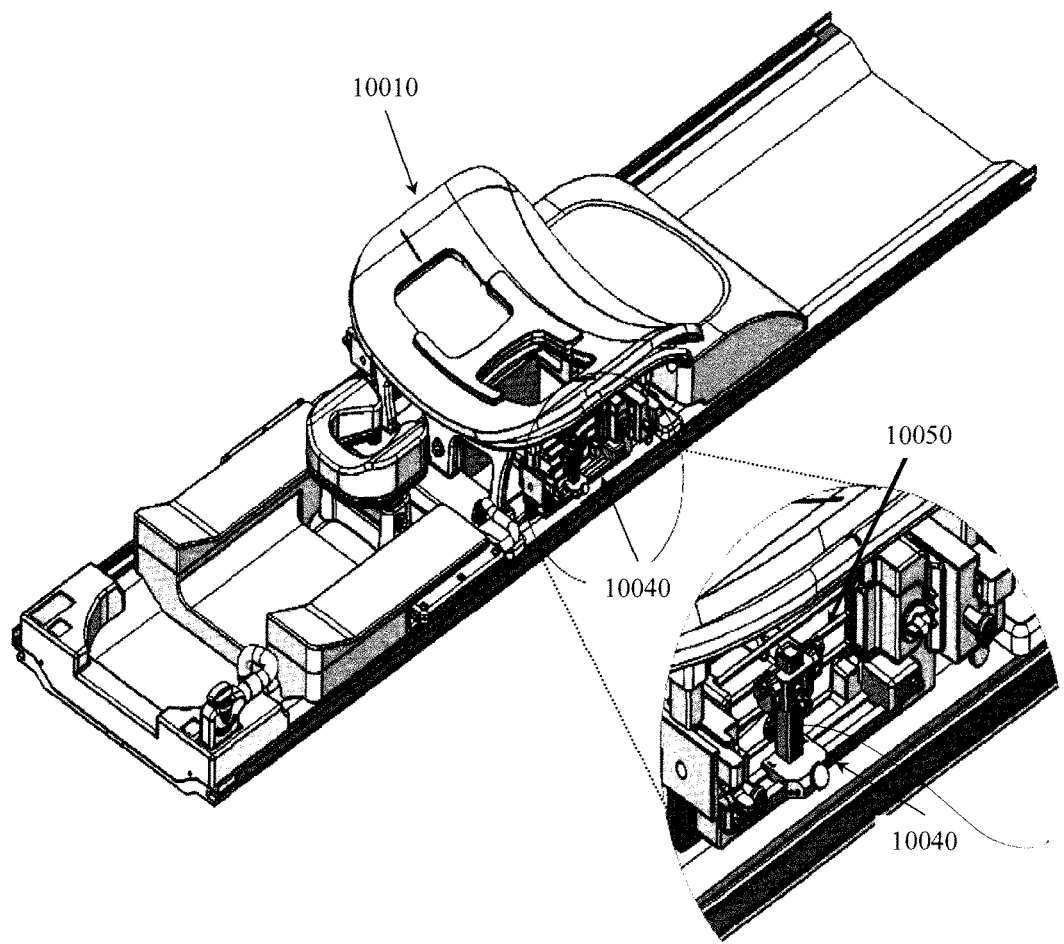
FIG. 29 illustrates a portion of an example reconfigurable MRI-guided surgical apparatus with a pillar and post assembly mounted and the side coil not mounted.

FIG. 29 illustrates apparatus 10010 and a pillar and post assembly 10040. Pillar and post assembly 10040 may include pressure rails 10050 that perform the role of applying pressure to the side of a breast. The pillar portion of pillar and post assembly 10040 may be movable in the horizontal (e.g., left/right) direction and the post portion of the pillar and post assembly 10040 may be movable in the vertical (e.g., up/down) direction. Pillar and post assembly 10040 may hold a needle or other surgical instrument. In one embodiment, pillar and post assembly 10040 may be computer controllable or may perform as a robot.

Figure 7:
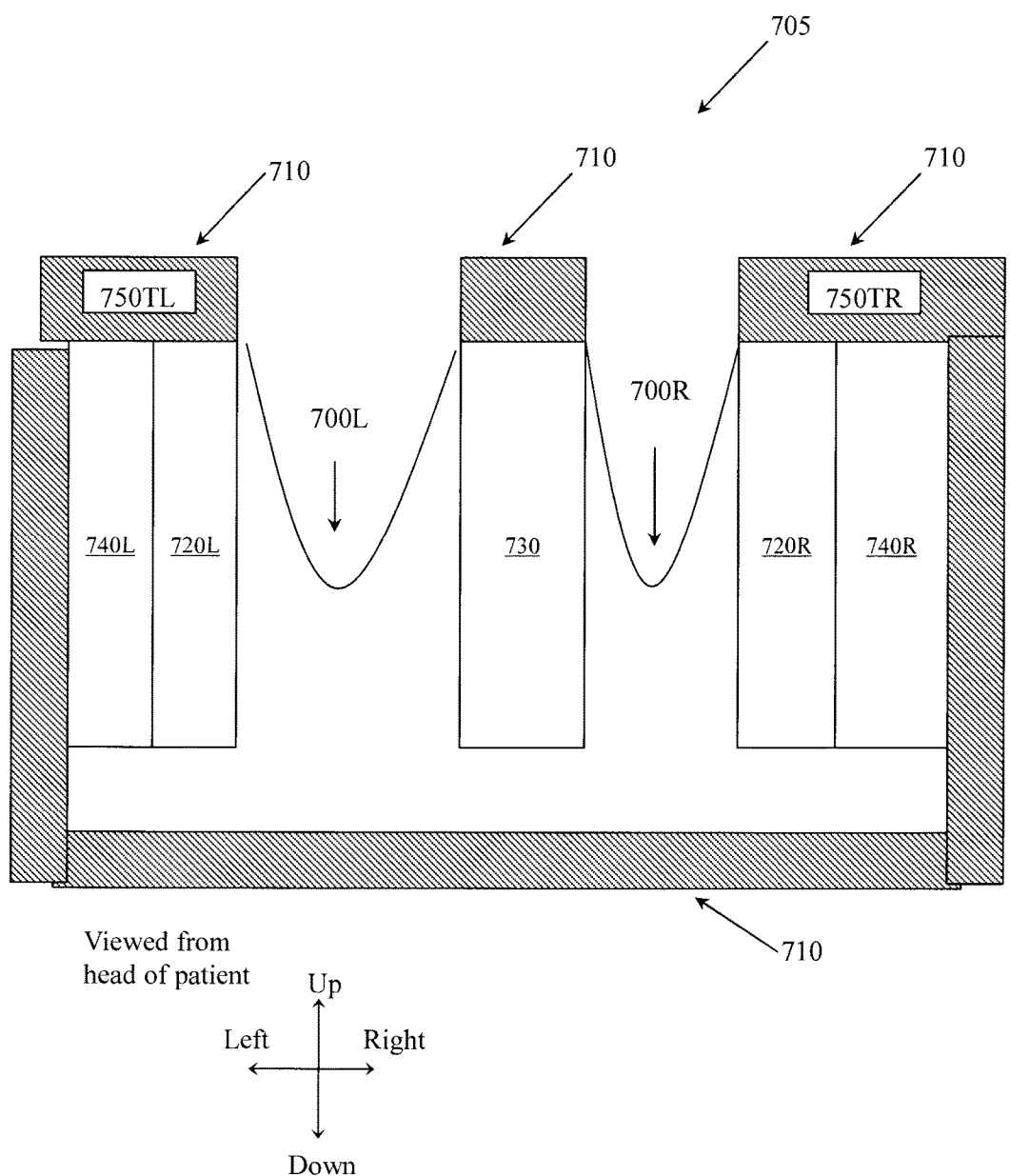
FIG. 7 illustrates a portion of an example reconfigurable MRI-guided surgical apparatus.
Figure 15:
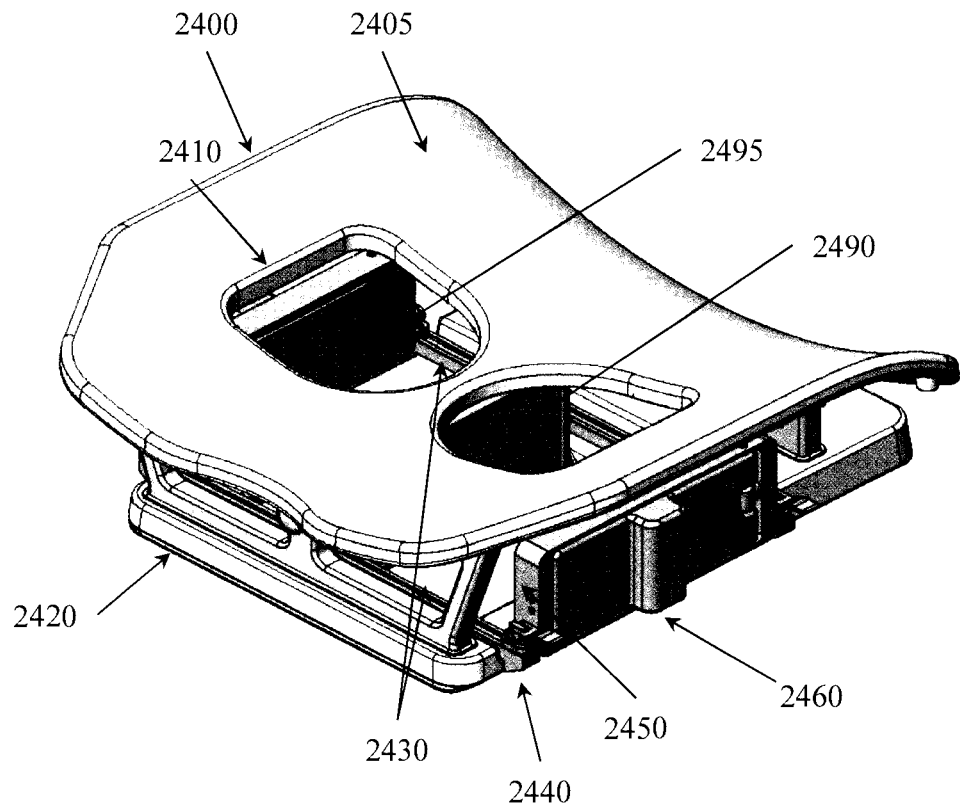
FIG. 15 illustrates an example reconfigurable MRI-guided surgical apparatus.

FIG. 7 illustrates portions of an apparatus 705 that may support a patient who is lying face down during an MRI-guided needle biopsy. FIG. 15 illustrates one example larger structure (e.g., breast coil apparatus 2400) with which apparatus 705 may be used. Apparatus 705, and other embodiments described herein, facilitate imaging a patient's breast to localize an area of interest in the breast. Apparatus 705, and other embodiments described herein, also facilitate readily and accurately obtaining a sample from the breast using a medical instrument (e.g., needle). The medical instrument may be guided by a medical instrument guidance assembly (e.g., biopsy plate, pillar and post assembly, robotic assembly). Accurate placement and acquisition may depend on adequate registration between the breast and the medical instrument guidance assembly.

Apparatus 705 is viewed from the head of the patient looking towards the feet of the patient. Apparatus 705 includes support structure 710 and two biopsy plates: a left biopsy plate 720L, and a right biopsy plate 720R. Apparatus 705 also includes two side coils: a left side coil 740L, and a right side coil 740R. Apparatus 705 also includes a central element 730 that may be used in compressing a breast. For example, left breast 700L may be compressed against central element 730 by moving left biopsy plate 720L towards the central element 730. Unlike conventional systems, when biopsy plate 720L is moved towards central element 730, left coil 740L may also be moved in with plate 720L. In one embodiment, coil 740L may be attached to plate 720L and they may move as a single unit. In another embodiment, coil 740L and plate 720L may be moved independently. In one embodiment, apparatus 705 may have either a biopsy plate (e.g., 720R) or a side coil (e.g., 740R). In this embodiment, the breast may be imaged using side coil 740R, then the side coil 740R may be removed, and the biopsy plate 720R mounted in apparatus 705 to perform the biopsy.

Apparatus 705 includes openings through which left breast 700L and right breast 700R of the patient may hang. Apparatus 705 may also include top coils and bottom coils. For example, apparatus 705 may include a left top coil 750TL and a right top coil 750TR. While two top coils are illustrated, a greater or lesser number of top coils could be employed.

Configuring apparatus 705 with the additional coils 750TL and 750TR may facilitate improving SNR in an MRI-guided needle biopsy both by increasing the number of coils available for imaging and by placing coils closer to the volume being imaged. However, note that as breast 700L is compressed by plate 720L or coil 740L towards element 730, breast 700L may be moved farther away from top left coil 750TL.

More generally, apparatus 705 is configured with a removable medical instrument guidance assembly, a coil, and structure for immobilizing the breast to facilitate registering a region of interest in the breast with the medical instrument guidance assembly.

Figure 8:
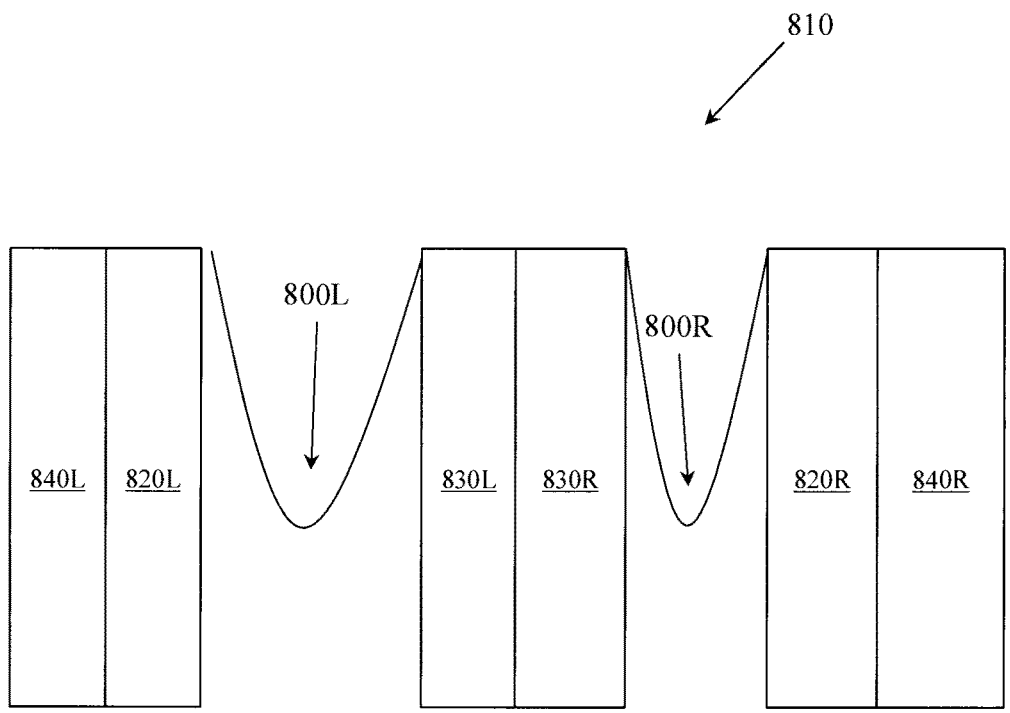
FIG. 8 illustrates a portion of an example reconfigurable MRI-guided surgical apparatus.
Figure 8:
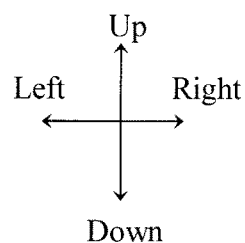

FIG. 8 illustrates portions of an apparatus 810 that may support a patient who is lying face down during an MRI-guided needle biopsy. Fixed support structures are not illustrated to facilitate focusing on the moveable pieces. Apparatus 810 is viewed from the head of the patient looking towards the feet of the patient. Apparatus 810 includes two biopsy plates: a left biopsy plate 820L and a right biopsy plate 820R. Apparatus 810 also includes two side coils: a left side coil 840L and a right side coil 840R. In one embodiment, apparatus 810 may have either side coils or biopsy plates. Apparatus 810 may first be configured with a side coil(s) to perform high SNR imaging. After the high SNR imaging is performed, the side coil(s) may be removed and the biopsy plate may be positioned. Apparatus 810 also includes two central coils (830R, 830L) that may, in addition to being used for imaging, also perform the function of central element 730 (FIG. 7). Apparatus 810 includes openings through which left breast 800L and right breast 800R of the patient may hang. Having the breasts hang down allows gravity to draw the breasts down, which may facilitate accessing areas of interest within a patient's breast near the chest wall. Apparatus 810 may also include top coils and bottom coils.

Configuring apparatus 810 with the additional coils 830L and 830R may facilitate improving SNR in an MRI-guided needle biopsy both by increasing the number of coils available for imaging and by placing coils closer to the volume being imaged. In one embodiment, coils 830L and 830R may be replaced by a single coil. As breast 800L is compressed towards coil 830L by plate 820L, breast 800L is positioned closer to coil 830L, which may improve image quality. Additionally, coil 840L may be repositioned to remain beside plate 820L as plate 820L is moved towards coil 830L to compress breast 800L. Repositioning the coil 840L to remain beside the plate 820L as the plate 820L is moved towards the coil 830L mitigates issues associated with conventional systems where the coils were fixed and could not move. When apparatus 810 is configured with both the plates and the side coils, the breast may be compressed by the biopsy plate, high SNR imaging may be performed, and then the side coils may be removed. The biopsy may then be performed through the biopsy plates.

Figure 9:
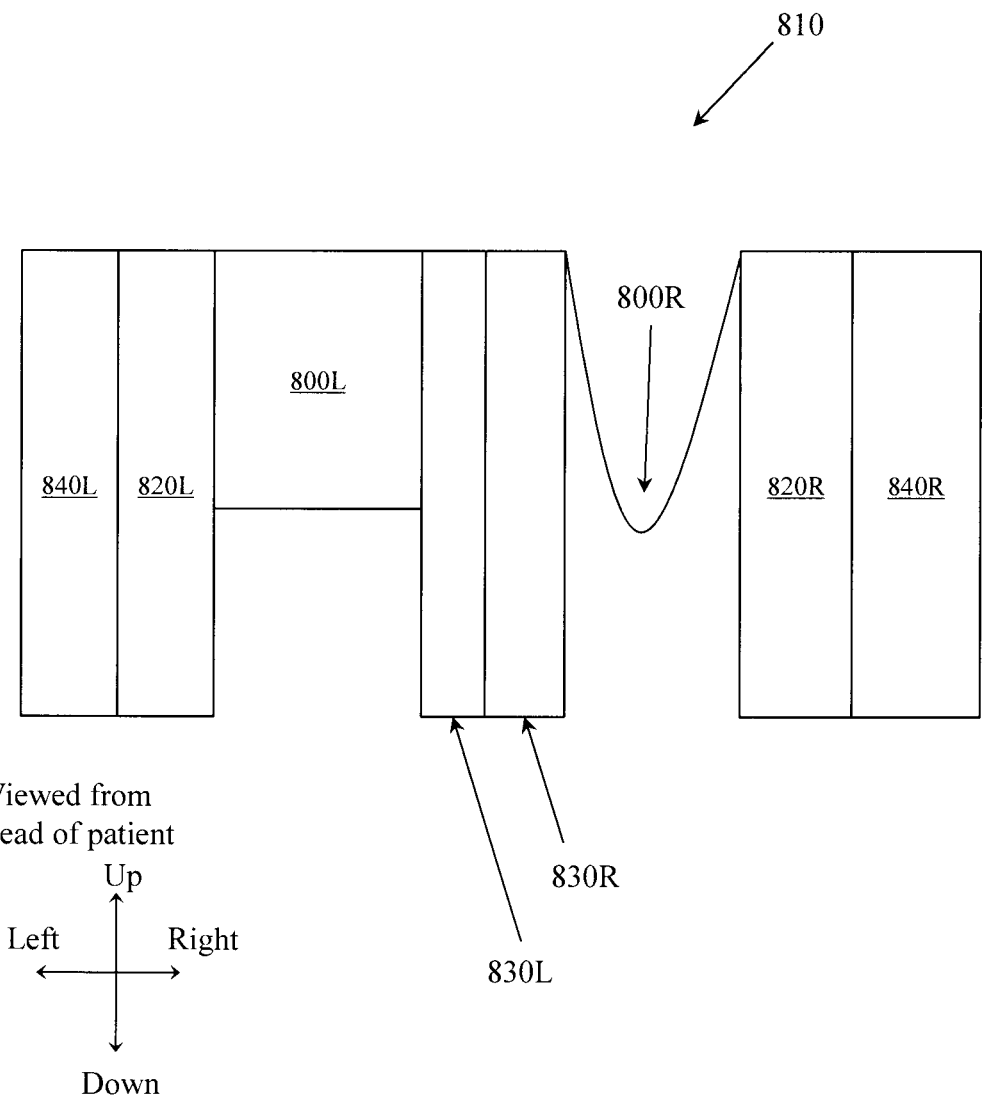
FIG. 9 illustrates a portion of an example reconfigurable MRI-guided surgical apparatus.

FIG. 9 illustrates portions of apparatus 810 after the left side biopsy plate 820L has been moved towards the left center coil 830L. Breast 800L has been compressed by the squeezing action of plate 820L and coil 830L. In one embodiment, when apparatus 810 is configured with either plate 820L or coil 830L, the breast may first be compressed by coil 830L, imaged, and then coil 830L may be removed and replaced with plate 820L or with another medical instrument guidance assembly (e.g., pillar and post). Compressing breast 800L facilitates holding breast 800L in a shape and position where a region of interest can be registered to a region in a biopsy plate or to a region accessible to a medical instrument guidance assembly. Registering a region of interest to a region in a biopsy plate means establishing a fixed spatial relationship between the two regions that will be maintained within a tolerance when the breast is held in the compressed state. Holding the breast in a fixed shape and position facilitates accurately inserting a needle into a region of interest. Compressing breast 800L also facilitates positioning left side coil 840L closer to the interior of the breast and positioning coil 830L closer to breast 800L.

Figure 10:
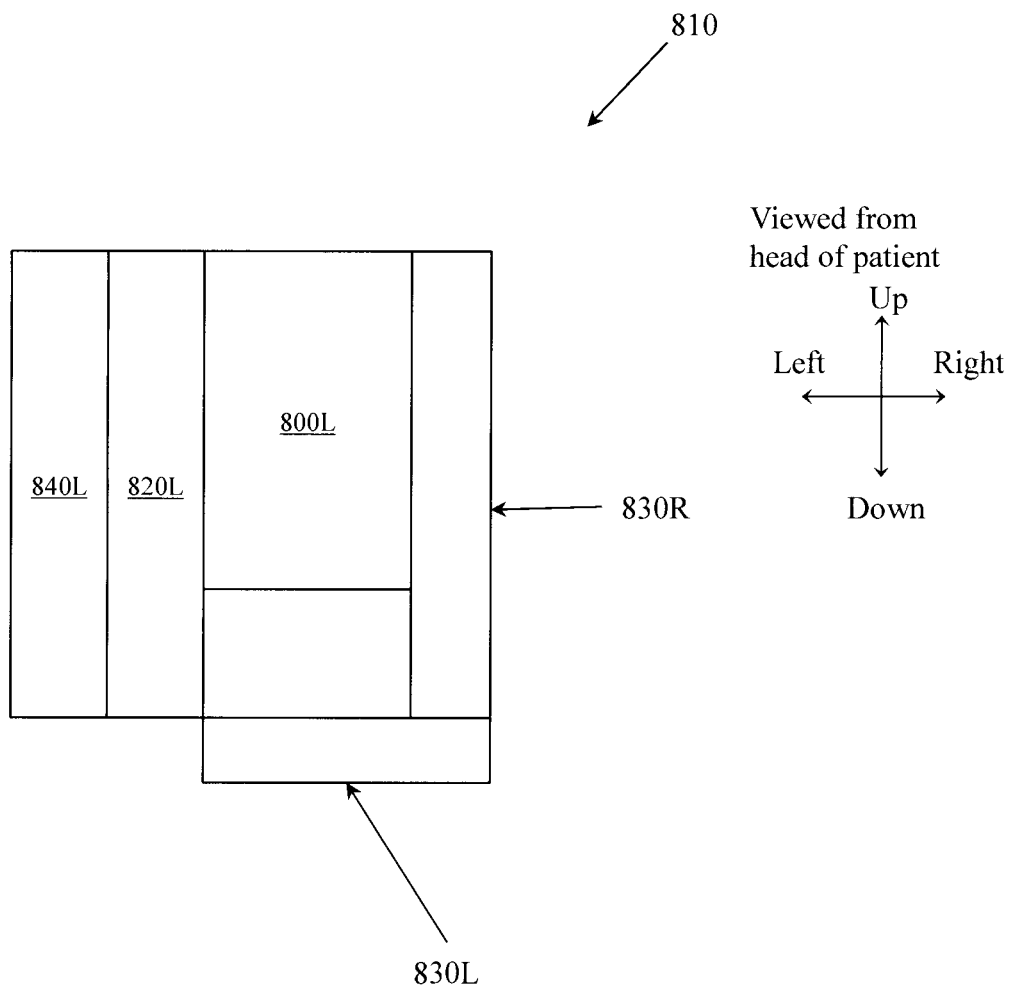
FIG. 10 illustrates a portion of an example reconfigurable MRI-guided surgical apparatus.

FIG. 10 illustrates portions of apparatus 810 after the left center coil 830L has been repositioned below left breast 800L. Left breast 800L has been compressed by moving left biopsy plate 820L towards right center coil 830R. In this configuration, apparatus 810 now provides three coils in close proximity to left breast 800L. Right center coil 830R is touching one side of breast 800L, left side coil 840L is closest to another side of breast 800L and left center coil 830L is positioned below breast 800L. Therefore, there are three coils positioned as close as practically possible to breast 800L. This may facilitate improving SNR which in turn may facilitate improving image quality. Having 830L perpendicular to 820L and 830R may also facilitate improving SNR by allowing for quadrature imaging. Left center coil 830L may have a hinge or other connector that facilitates repositioning 830L from its initial vertical orientation to a subsequent horizontal position. While coil 830L is illustrated in a horizontal position, other orientations may be employed. While FIG. 9 illustrates two center coils 830L and 830R, in some embodiments there would only be a single center coil. In some embodiments where there are two center coils, only one coil may be used at a time.

Figure 11:
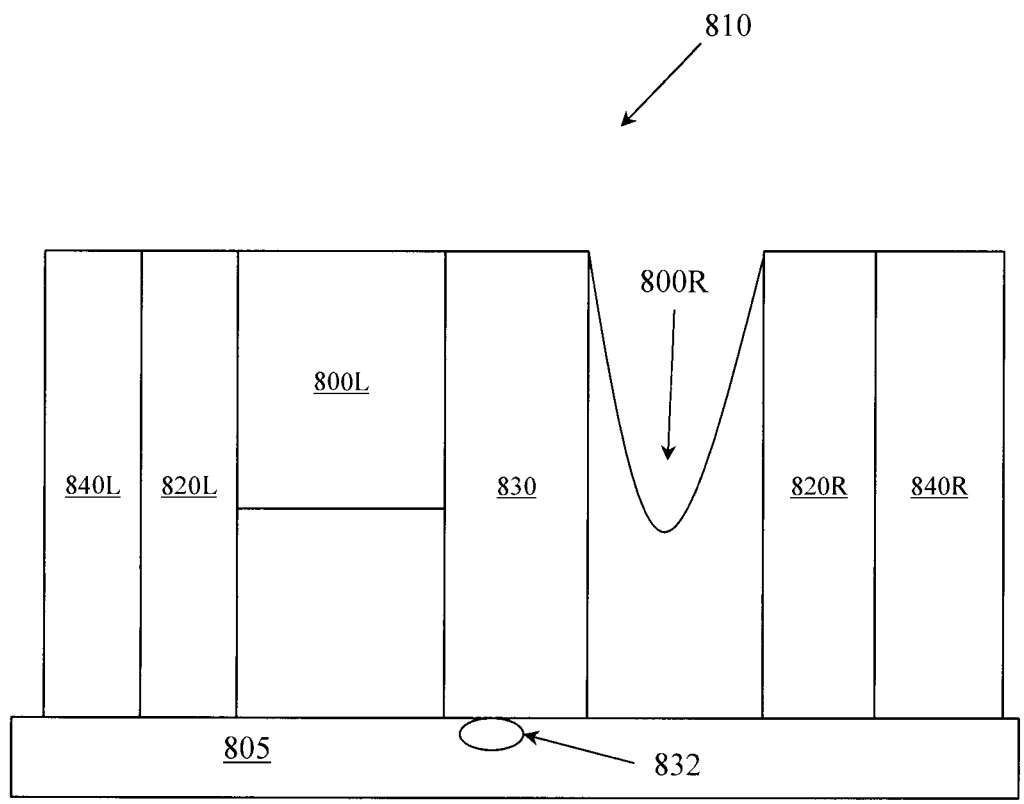
FIG. 11 illustrates a portion of an example reconfigurable MRI-guided surgical apparatus.
Figure 11:
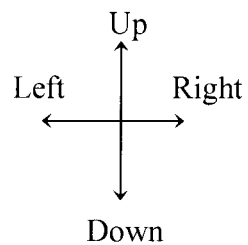

FIG. 11 illustrates another embodiment of portions of apparatus 810. In this embodiment, rather than having two central coils 830L and 830R, there is just a single central coil 830. Apparatus 810 may include a guide 805. Central coil 830 may be attached to guide 805 by, for example, a hinge 832 or other connector that allows central coil 830 to rotate from a vertical orientation to a horizontal orientation. While rotating central coil 830 is described, more generally central coil 830 can be repositioned from one position to another to facilitate keeping central coil 830 in a position that contributes to improving SNR.

Figure 12:
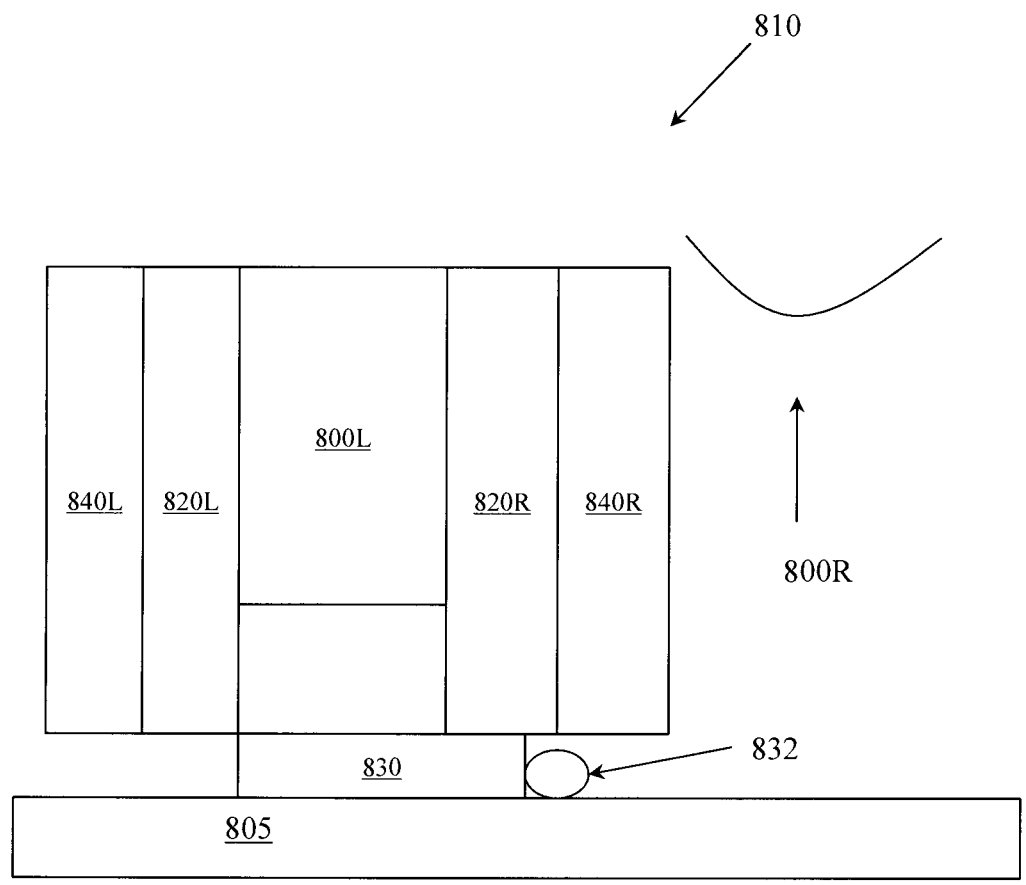
FIG. 12 illustrates a portion of an example reconfigurable MRI-guided surgical apparatus.

FIG. 12 illustrates portions of apparatus 810 after the central coil 830 has been repositioned below breast 800L. Breast 800R has been displaced upwards to allow right biopsy plate 820R and right side coil 840R to be moved into the center region to facilitate higher SNR imaging of breast 800L. Breast 800L is illustrated being compressed between left biopsy plate 820L and right biopsy plate 820R. In one embodiment, rather than repositioning central coil 830 under breast 800L, the central coil may be repositioned away from breast 800L (e.g., under breast 800R).

Figure 13:
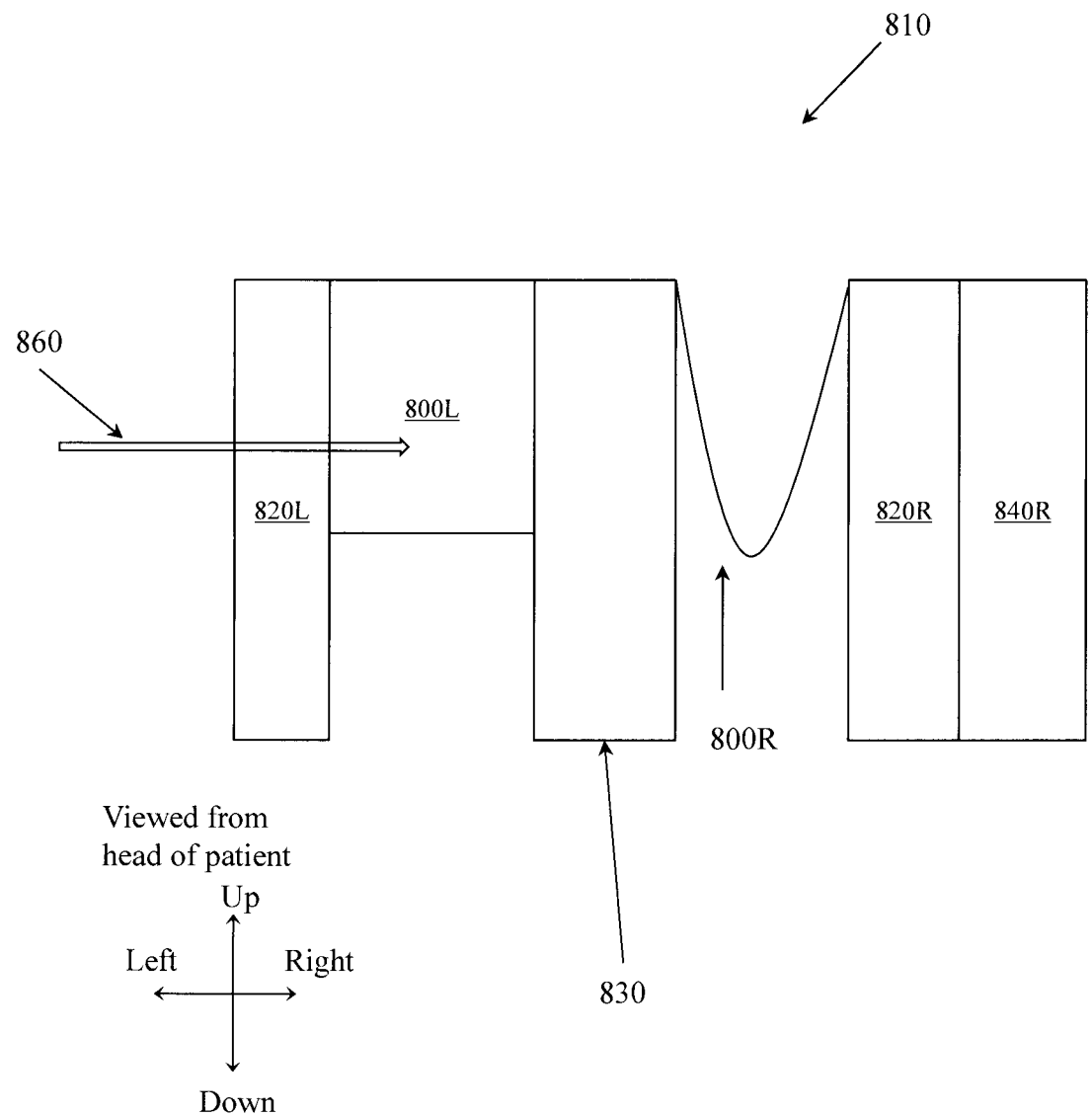
FIG. 13 illustrates a portion of an example reconfigurable MRI-guided surgical apparatus.

FIG. 13 illustrates a needle 860 being inserted laterally into breast 800L. To insert the needle 860 laterally, the left side coil 840L has been repositioned. Left side coil 840L may, in one example, be removed.

Figure 14:
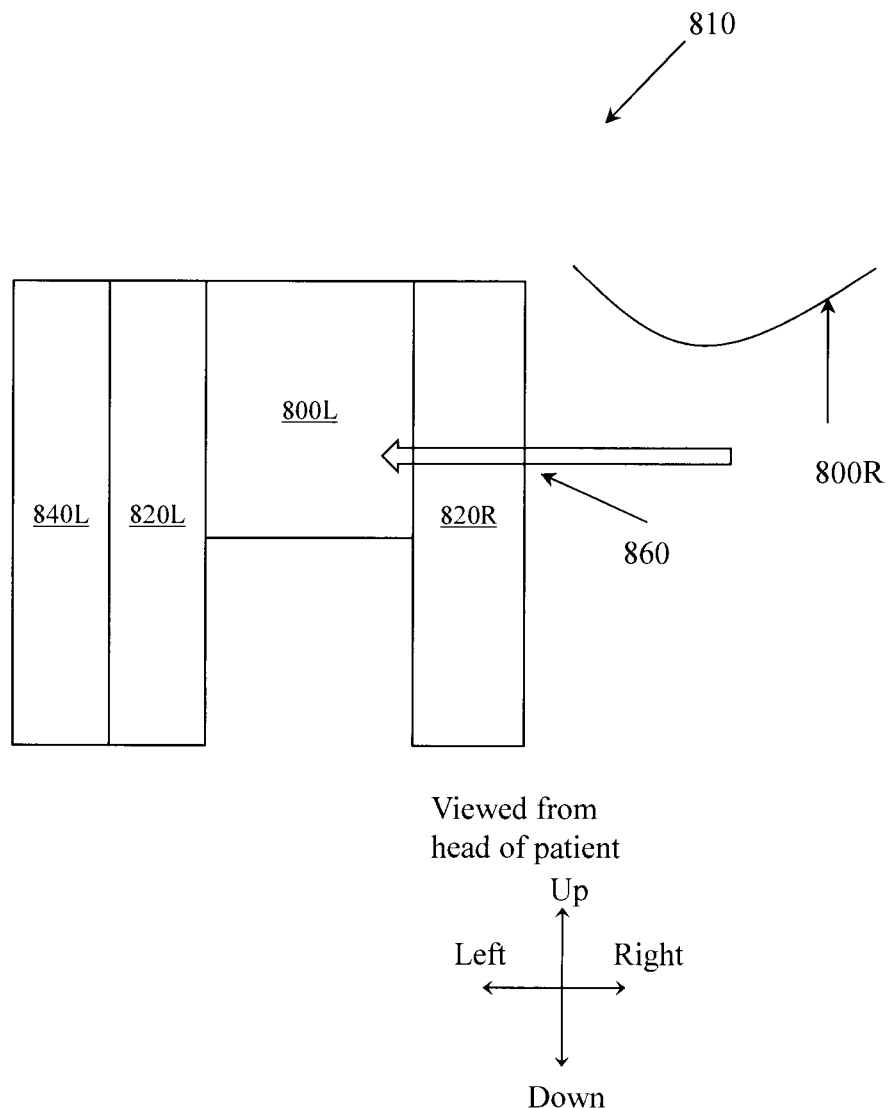
FIG. 14 illustrates a portion of an example reconfigurable MRI-guided surgical apparatus.

FIG. 14 illustrates needle 860 being inserted medially into breast 800L. To insert the needle 860 medially, the right side coil 840R may be repositioned or removed, or center coil 830R may be repositioned. Example apparatus facilitate repositioning (e.g., removing) side coils to provide access to biopsy plates or other medical instrument guidance assemblies for either medial or lateral insertion. In different embodiments a side coil may accordion like a bi-fold door to facilitate repositioning, may be repositioned in other ways, or may be removable from an apparatus. In this configuration, right side coil 840R has been moved out of the way and right side biopsy plate 820R is used to hold the breast 800L in place.

FIG. 15 illustrates an apparatus 2400 for use in an MRI-guided medical procedure on a patient's breast. Apparatus 2400 includes a support structure 2405 that is configured to support a patient in a face-down prone position where a breast is positioned in a first free hanging pre-imaging position. The breast would hang down through, for example, opening 2410.

Apparatus 2400 also includes an immobilization structure 2420 that facilitates repositioning the breast into an immobilized position suitable for MRI and for medical instrument access. In one embodiment, the immobilization structure 2420 includes a biopsy plate 2450, a pressure plate 2490, and at least two MRI coils. One MRI coil 2460 is positioned together with biopsy plate 2450. A second MRI coil may be positioned together with a second biopsy plate 2495. In one embodiment, apparatus 2400 may have either biopsy plate 2450 or coil 2460. Biopsy plate 2450 and coil 2460 may be interchangeably mounted in apparatus 2400. In one embodiment, pressure plate 2490 may include an RF coil. In one embodiment, coil 2460 may be attached to immobilization structure 2420. In one embodiment, coil 2460 is removable.

In one embodiment, an MRI coil is configured to be repositioned from a first position associated with the free hanging pre-imaging position to a second position associated with the immobilized position. Repositioning the MRI coil facilitates improving SNR by placing the coil closer to the breast being imaged. Thus, the SNR associated with signal received from the breast through the MRI coil is improved by repositioning the coil from the first position to the second position. Since the breast is being imaged as part of an MRI-guided procedure (e.g., needle biopsy), the immobilization structure 2420 is configured to allow removal of the biopsy plate 2450 after a procedure so that a new, sterile plate may be inserted. The immobilized position may be achieved by moving biopsy plate 2450 towards pressure plate 2490 in an amount sufficient to trap a breast hanging down between the biopsy plate 2450 and the pressure plate 2490. A force sufficient to immobilize the trapped breast may be applied.

In one embodiment, the immobilization structure 2420 is configured to hold MRI coils parallel to each other in a position suitable for performing bilateral imaging when the breast is held in the immobilized position. Holding MRI coils parallel may be achieved by, for example, configuring immobilization structure 2420 with rails 2430 upon which the MRI coils may slide. Rails 2430 may also be used to mount, move, and lock in place the biopsy plate 2450 or other medical instrument guidance assemblies. While rails 2430 are described, other structures (e.g., tracks, guides) may be employed to hold the MRI coils in a parallel position and to allow the MRI coils to move towards and away from a breast.

In one embodiment, the immobilization structure 2420 is configured to hold MRI coils perpendicular to each other in a position suitable for performing unilateral imaging when the breast is held in the immobilized position. This may include rotating an MRI coil from an upright position that is parallel to another MRI coil to a flat position. Thus, immobilization structure 2420 may have a joint that facilitates repositioning a coil from the upright position to the flat position. When the two coils are perpendicular to each other, unilateral imaging may be performed using high resolution imaging. When high resolution imaging is employed, an SNR associated with signal received from the breast through the MRI coils during unilateral imaging may be superior to an SNR associated with signal received from the breast through the MRI coils during bilateral imaging.

In one embodiment, the MRI coil 2460 may be moved away from biopsy plate 2450. In this open configuration, biopsy plate 2450 may be accessed to facilitate applying a medical instrument (e.g., biopsy needle) through biopsy plate 2450 to reach a breast positioned between biopsy plate 2450 and pressure plate 2490. In one embodiment, the coil 2460 may be removed from the apparatus 2400.

Figure 16:
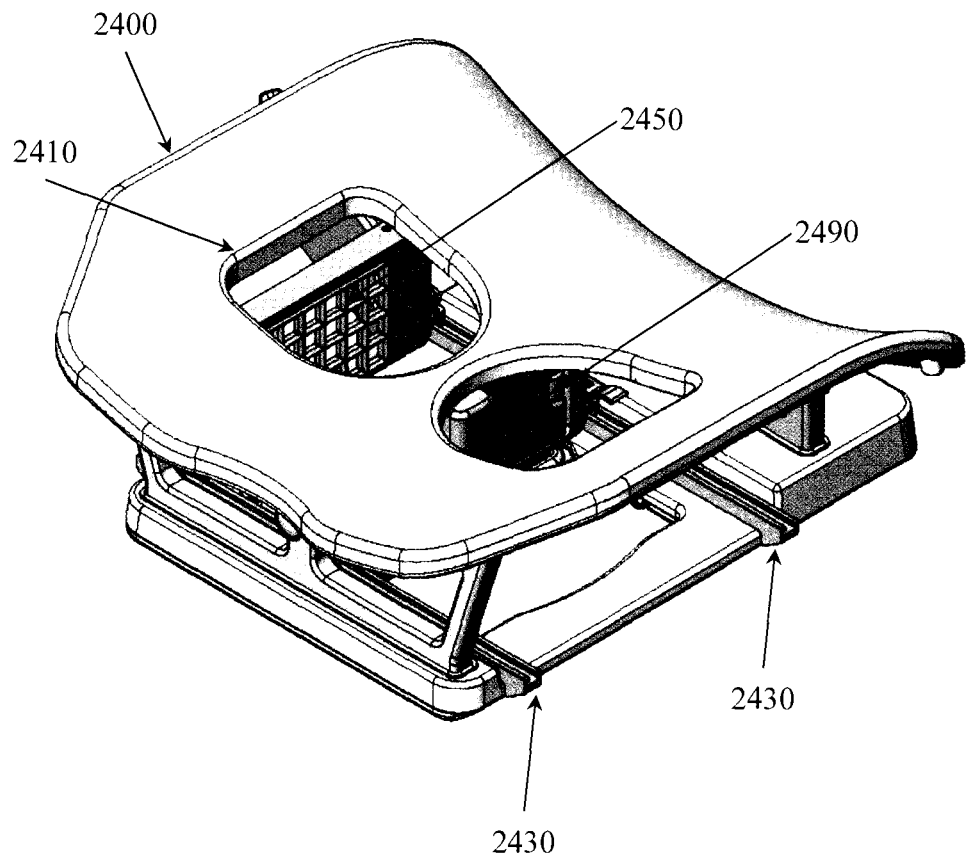
FIG. 16 illustrates an example reconfigurable MRI-guided surgical apparatus.

FIG. 16 illustrates apparatus 2400 from a different viewpoint. In this view, rails 2430 are more clearly visible. While FIGS. 15 and 16 illustrate one example model, FIGS. 17-24 illustrate various component parts of an inner assembly being reconfigured during the lifecycle of an MRI-guided medical procedure.

Figure 17:
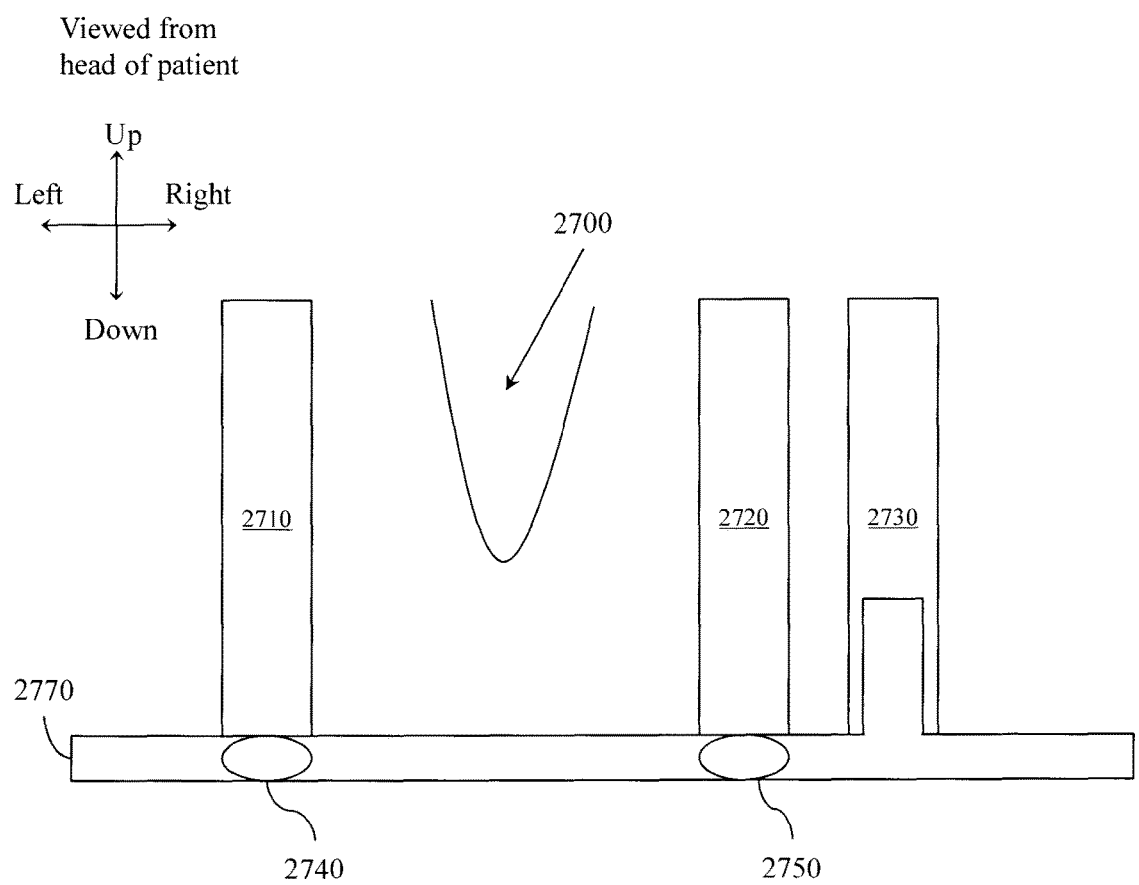
FIG. 17 illustrates a portion of an example reconfigurable MRI-guided surgical apparatus.

FIG. 17 illustrates a portion of an inner assembly for use with a breast coil in an MRI-guided medical procedure on a patient's breast. FIG. 17 illustrates a breast 2700 disposed between a brace assembly 2710 and a medical instrument guidance assembly 2720. The medical instrument guidance assembly 2720 is attached to a guide 2770 by a connector 2750. The brace assembly 2710 is attached to the guide 2770 by a rotation point 2740. The breast 2700 is also disposed between the brace assembly 2710 and a side coil 2730. In one embodiment, guide 2770 may correspond to rails 2430 (FIG. 16). In one embodiment, the apparatus may be configured so that side coil 2730 is removable from the apparatus to allow access to medical instrument guidance assembly 2720. In one embodiment, the apparatus may have only one of the medical instrument guidance assembly 2720 or the side coil 2730 at a time. In this embodiment, the side coil 2730 and assembly 2720 may be designed to produce the same pressure profile on the breast 2700 when located in the same position. Thus, the side coil 2730 may be used to compress the breast 2700 for imaging, and then the assembly 2720 may be used to compress the breast 2700 during a surgical procedure.

The side coil 2730 is configured to participate in MRI of the breast 2700. Thus, in one embodiment, the side coil 2730 may generate RF energy to be applied to the breast 2700 during the MRI-guided medical procedure. In another embodiment, the side coil 2730 may receive NMR signals from the breast 2700 during the MRI-guided medical procedure.

The medical instrument guidance assembly 2720 is configured to contact the breast 2700. The medical instrument guidance assembly 2720 is also configured to be inserted into and removed from a larger apparatus (e.g., breast coil) housing the inner assembly. In one embodiment, the medical instrument guidance assembly 2720 may correspond to biopsy plate 2450 (FIG. 25) and the larger apparatus may correspond to breast coil 2400. In another embodiment, the medical instrument guidance assembly 2720 may correspond to a pillar and post apparatus 10040 (FIG. 29).

The brace assembly 2710 is also configured to contact the breast 2700. For example, the medical instrument guidance assembly 2720 could be moved to the left to contact breast 2700 from one side and the brace assembly 2710 could be moved to the right to contact breast 2700 from the opposite side. Alternatively, the entire assembly could be moved to the right until brace assembly 2710 was in contact with breast 2700 and then the medical instrument guidance assembly 2720 could be moved to the left to contact breast 2700. Other movements may also be employed.

Guide 2770 may movably and lockably position the medical instrument guidance assembly 2720, the side coil 2730, and/or the brace assembly 2710 in both an imaging mode and a procedure mode. Being configured to "movably and lockably position" an item means that guide 2770 can be used to facilitate moving the item from a first position to a second position and fixing the item at either position. The movement may be guided by rails, for example. In one example, the locking may be performed by a clamp. Thus, the medical instrument guidance assembly 2720, the side coil 2730, and the brace assembly 2710 may be movably engaged to the guide 2770. In one embodiment, the guide 2770 may be configured for positioning the medical instrument guidance assembly 2720 on a first side of the breast 2700 and for positioning the brace assembly 2710 on a second, opposing side of the breast 2700 so that the assembly 2710 and assembly 2720 can be used to apply to the breast 2700 a force sufficient to hold the breast 2700 against the medical instrument guidance assembly 2720 in a fixed spatial relationship having a desired tolerance during the MRI-guided medical procedure. The tolerance may be, for example, one millimeter. Other clinically-relevant tolerances may be employed.

The guide 2770 may have a connector 2750 for removably attaching the medical instrument guidance assembly 2720. In different embodiments, different types of connectors may be employed.

The guide 2770 may control and allow movement of the side coil 2730 from a first position to a second position. Being configured to "control and allow movement" of an item means that guide 2770 can provide the mechanical structure (e.g., rails) that allow an item to move back and forth and that also define the possible positions to which the item can be moved. In one example, the first position may be farther from the breast 2700 and the second position may be closer to the breast 2700. Thus, a signal received from the breast 2700 by the side coil 2730 in the first position during the MRI-guided surgical procedure may yield a first SNR and a signal received from the breast 2700 by the side coil 2730 in the second position during the MRI-guided surgical procedure may yield a second, higher SNR. After the imaging is complete, the side coil 2730 may be removed by, for example, sliding the side coil 2730 off the guide 2770.

In one embodiment, the guide 2770 may control and allow movement of the side coil 2730 to a third position by removing the side coil. The third position may facilitate accessing the medical instrument guidance assembly 2720 for a medical instrument to be inserted into the breast through the medical instrument guidance assembly 2720.

In one embodiment, the medical instrument guidance assembly 2720 may be a biopsy plate and the medical instrument may be a needle suitable for performing a needle biopsy. Since access from either side of breast 2700 may be desired, in one embodiment, the brace assembly 2710 may include a second medical instrument guidance assembly and a second side coil.

Figure 18:
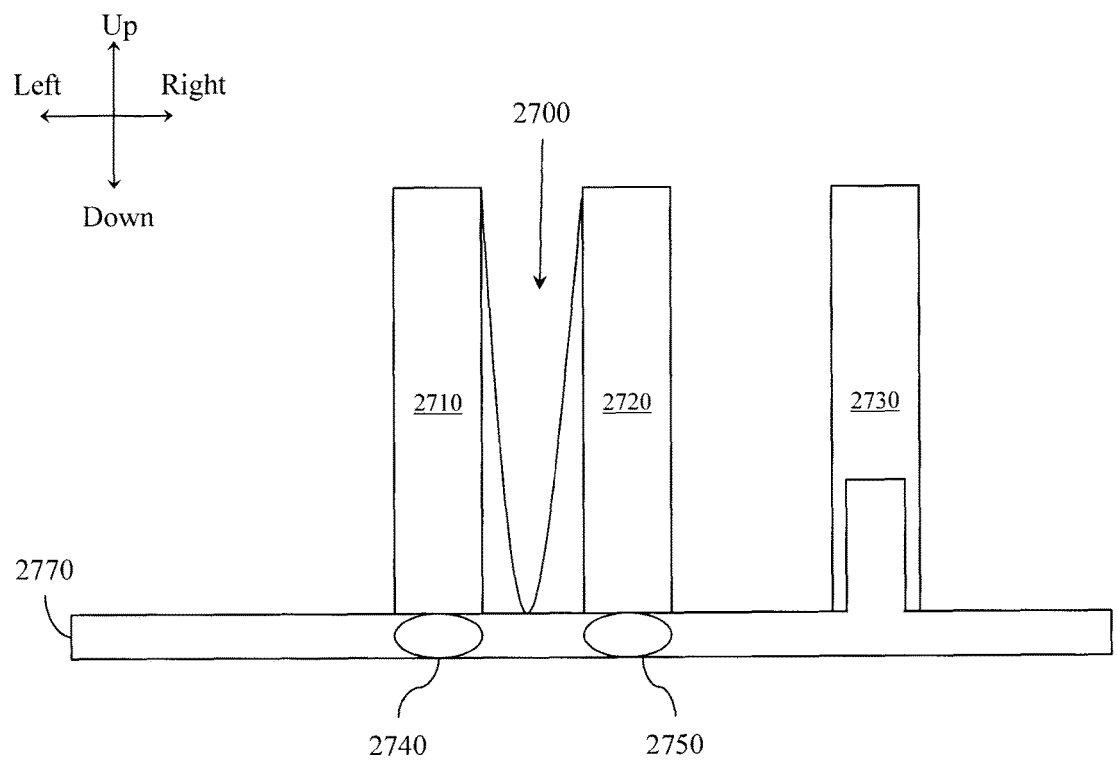
FIG. 18 illustrates a portion of an example reconfigurable MRI-guided surgical apparatus.

FIG. 18 illustrates the breast 2700 after it has been contacted and immobilized by the brace assembly 2710 and the medical instrument guidance assembly 2720. The brace assembly 2710 and the medical instrument guidance assembly 2720 cooperate to apply a force sufficient to immobilize breast 2700 to within a desired tolerance. In one embodiment, the tolerance may be less than 1 millimeter of movement throughout the medical procedure. In different embodiments, different tolerances may be employed.

Figure 19:
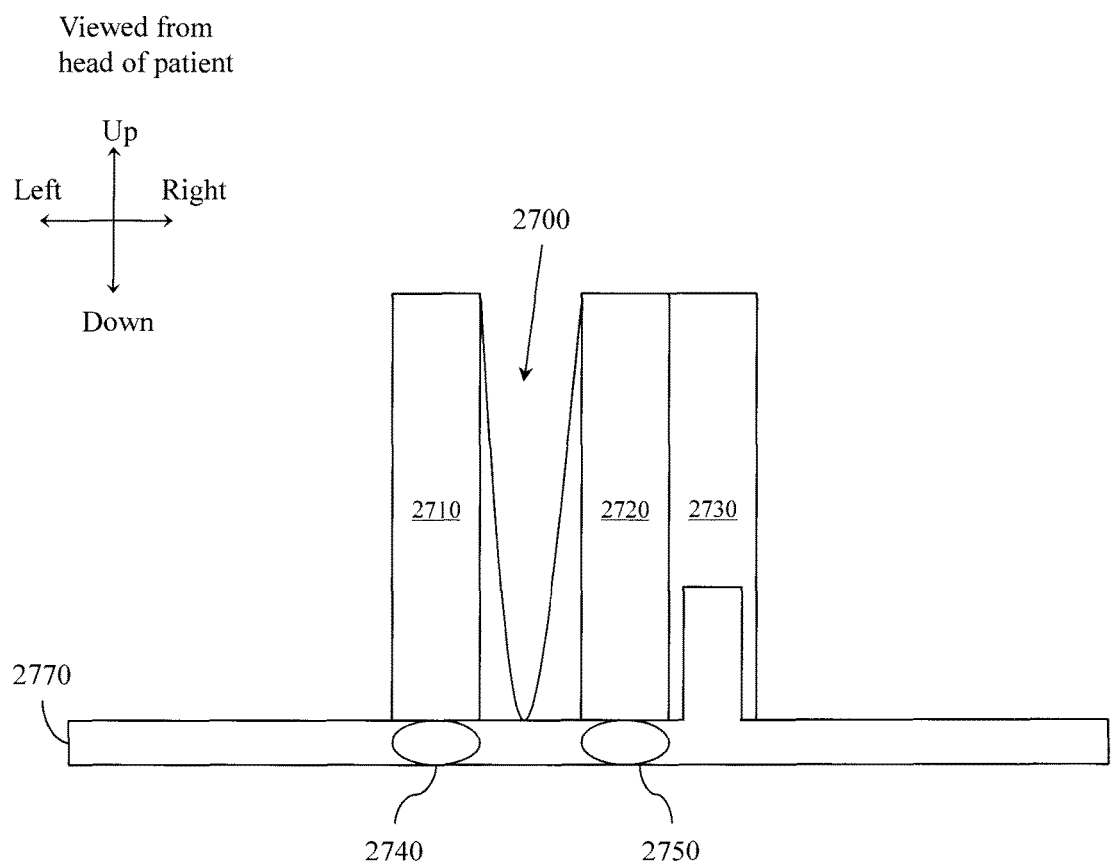
FIG. 19 illustrates a portion of an example reconfigurable MRI-guided surgical apparatus.

FIG. 19 illustrates side coil 2730 after it has been moved closer to breast 2700. The SNR of a signal received from breast 2700 will likely be higher when side coil 2730 is closer to breast 2730 as illustrated in FIG. 19 than it would be when the side coil 2730 is farther from breast 2730 as illustrated in FIG. 18. In one embodiment, side coil 2730 may be used first without assembly 2720 to perform high SNR imaging. Side coil 2730 may then be removed and replaced with assembly 2720.

Figure 20:
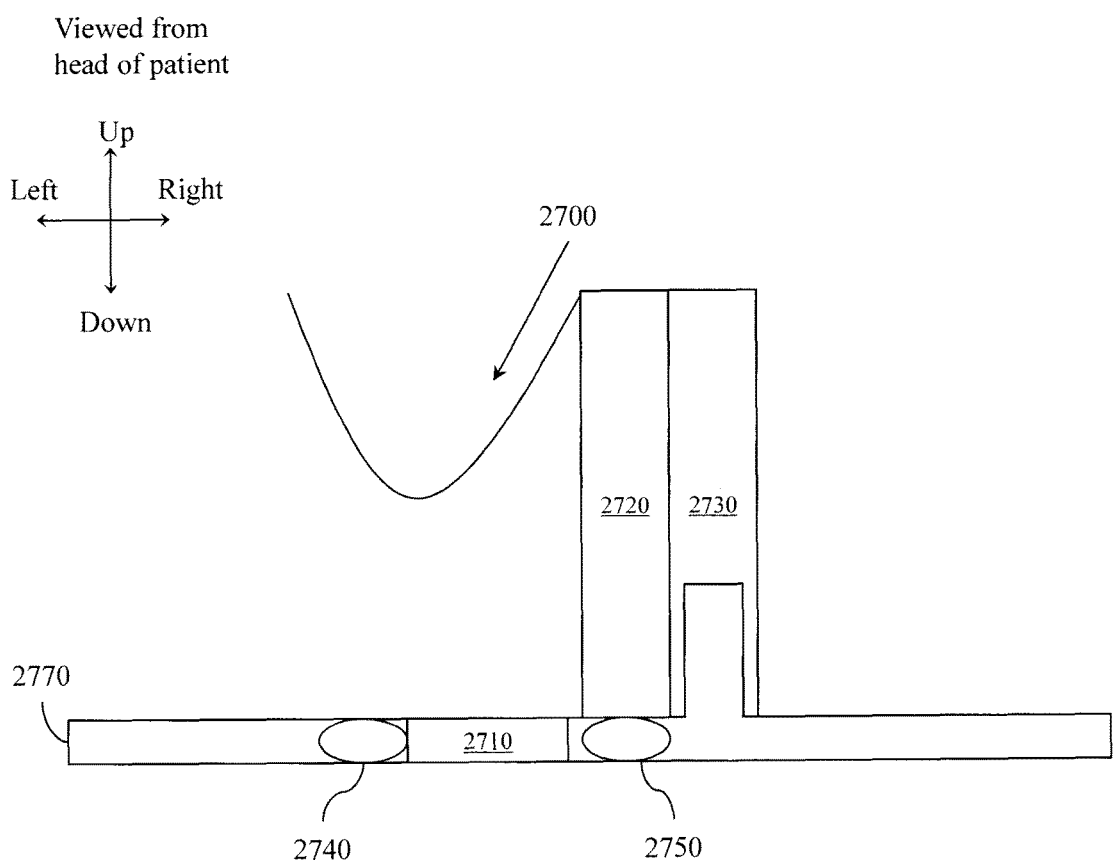
FIG. 20 illustrates a portion of an example reconfigurable MRI-guided surgical apparatus.

FIG. 20 illustrates brace assembly 2710 after it has been rotated from its original position to a subsequent position. In one embodiment, the guide 2770 may have a rotation point 2740 to control and allow movement of the brace assembly 2710 from the original position to the subsequent position. The first position may be used for bilateral imaging and the subsequent position may be used for unilateral imaging. The rotation point 2740 may be, for example, a hinge, a gimbal, or other device that permits rotation or relocation from the upright position illustrated in FIG. 19 to the horizontal position illustrated in FIG. 20. While a perfectly vertical orientation for brace assembly 2710 is illustrated in FIG. 19, and while a perfectly horizontal orientation is illustrated for brace 2710 in FIG. 20, guide 2770 and rotation point 2740 may produce other orientations for brace assembly 2710. This configuration illustrates an intermediate position before the breast 2700 has been compressed between the two sides.

Figure 21:
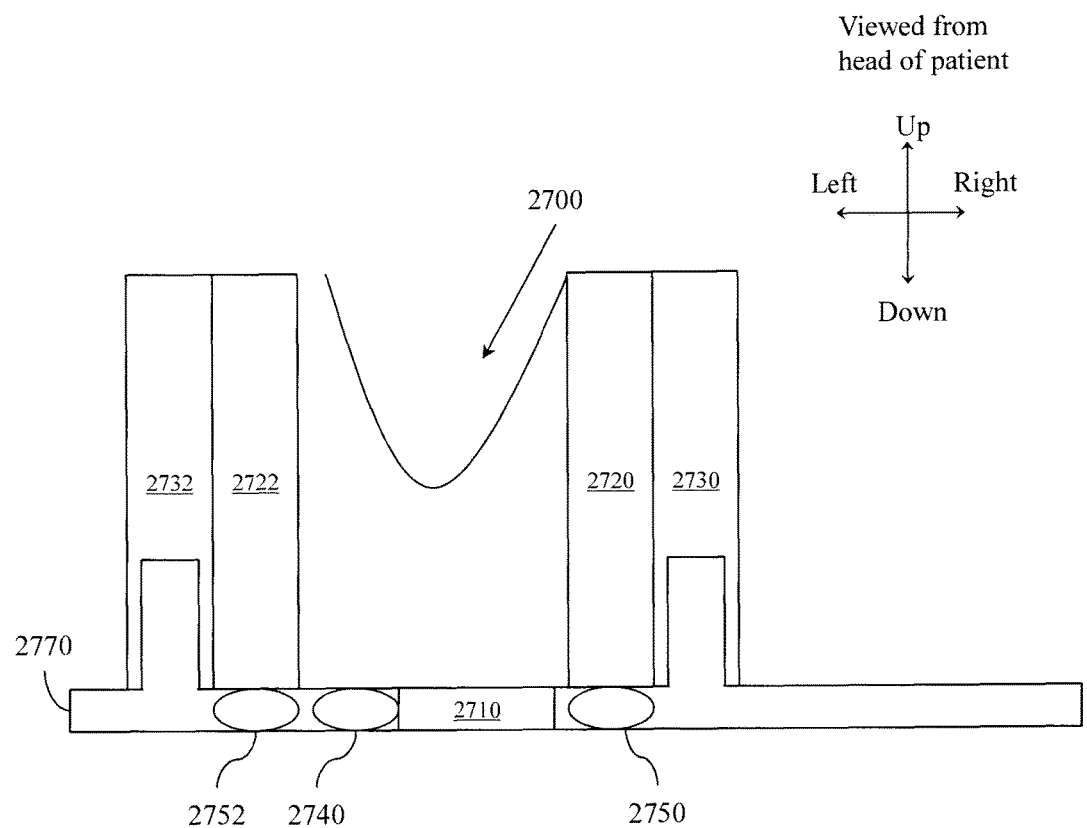
FIG. 21 illustrates a portion of an example reconfigurable MRI-guided surgical apparatus.

FIG. 21 illustrates the inner assembly configured with a second medical instrument guidance assembly 2722 and a second side coil 2732. In this embodiment, the guide 2770 may movably and lockably position the second medical instrument guidance assembly 2722 in both the imaging mode and the procedure mode. Thus, the second medical instrument guidance assembly 2722 may be movably engaged to the guide 2770. The guide 2770 may have a second connector 2752 for removably attaching the second medical instrument guidance assembly 2722 to the guide 2770.

In this embodiment, the guide 2770 may be configured for positioning the second medical instrument guidance assembly 2722 on the second, opposing side of the breast 2700 to facilitate applying to the breast 2700 a force sufficient to hold the breast 2700 against the medical instrument guidance assembly 2720 and the second medical instrument guidance assembly 2722 in a fixed spatial relationship having a desired tolerance during the MRI-guided medical procedure.

FIG. 21 also illustrates the second side coil 2732. The guide 2770 facilitates moving and locking the second side coil 2732 in position in both the imaging mode and the procedure mode. The guide 2770 controls and allow movement of the second side coil 2732 from an initial position to a subsequent position. Moving second side coil 2732 facilitates having a signal received from the breast 2700 by the second side coil 2732 in the initial position during the MRI-guided surgical procedure yield an initial SNR. Moving second side coil 2732 further facilitates having a signal received from breast 2700 by the second side coil 2732 in the subsequent position during the MRI-guided surgical procedure yield a higher SNR.

In different embodiments, the guide 2770 may control and allow movement of the second side coil 2732 to an open position. The open position provides access to the second medical instrument guidance assembly 2722 for the medical instrument to be inserted into the breast 2700 through the second medical instrument guidance assembly 2722. In one embodiment, guide 2770 may allow the easy removal of second side coil 2732 after imaging to allow access to assembly 2722.

Figure 22:
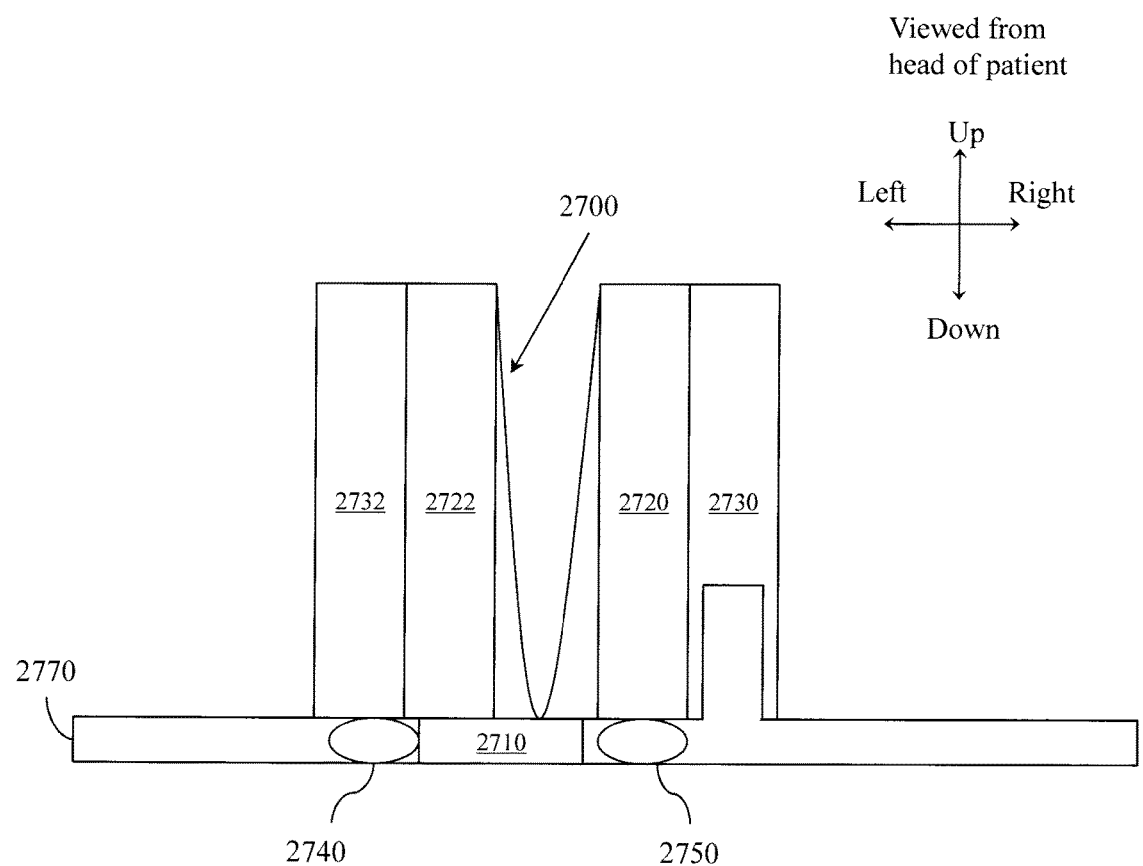
FIG. 22 illustrates a portion of an example reconfigurable MRI-guided surgical apparatus.

FIG. 22 illustrates how the guide 2770 can facilitate switching from bilateral imaging to unilateral imaging during an MRI-guided procedure. The switching is possible when the guide 2770 controls and allow repositioning (e.g., rotation) of the brace assembly 2710 from a vertical position used in bilateral imaging to a horizontal position used in unilateral imaging. As described above, the rotation or other repositioning of assembly 2710 is accomplished by rotation point 2740.

With the brace assembly 2710 in the horizontal position, a breast coil housing the inner assembly may perform quadrature imaging using at least one of the side coils 2730 and 2732 and a coil in the brace assembly 2710 when positioned perpendicular to the at least one side coil.

In one embodiment, the guide 2770 may hold the medical instrument guidance assembly 2720, the brace assembly 2710, and the side coil 2730 in a set of parallel planes. In another embodiment, the guide 2770 may hold the medical instrument guidance assembly 2720, the second medical instrument guidance assembly 2722, the side coil 2730, the second side coil 2732, and the brace assembly 2710 in a set of parallel planes.

In different embodiments, the guide 2770 may also hold the brace assembly 2710 in a position perpendicular to the medical instrument guidance assembly 2720, the side coil 2730, the second medical instrument guidance assembly 2732, or the second side coil 2732.

The inner assembly illustrated in FIGS. 17-22 may be positioned in a breast coil having a top portion and a bottom portion as illustrated in FIGS. 15-16. In different embodiments, the top portion may have one or more coils positioned and configured for performing MRI of the breast. The bottom portion may also be configured with one or more coils positioned and configured for performing MRI of the breast.

Figure 23:
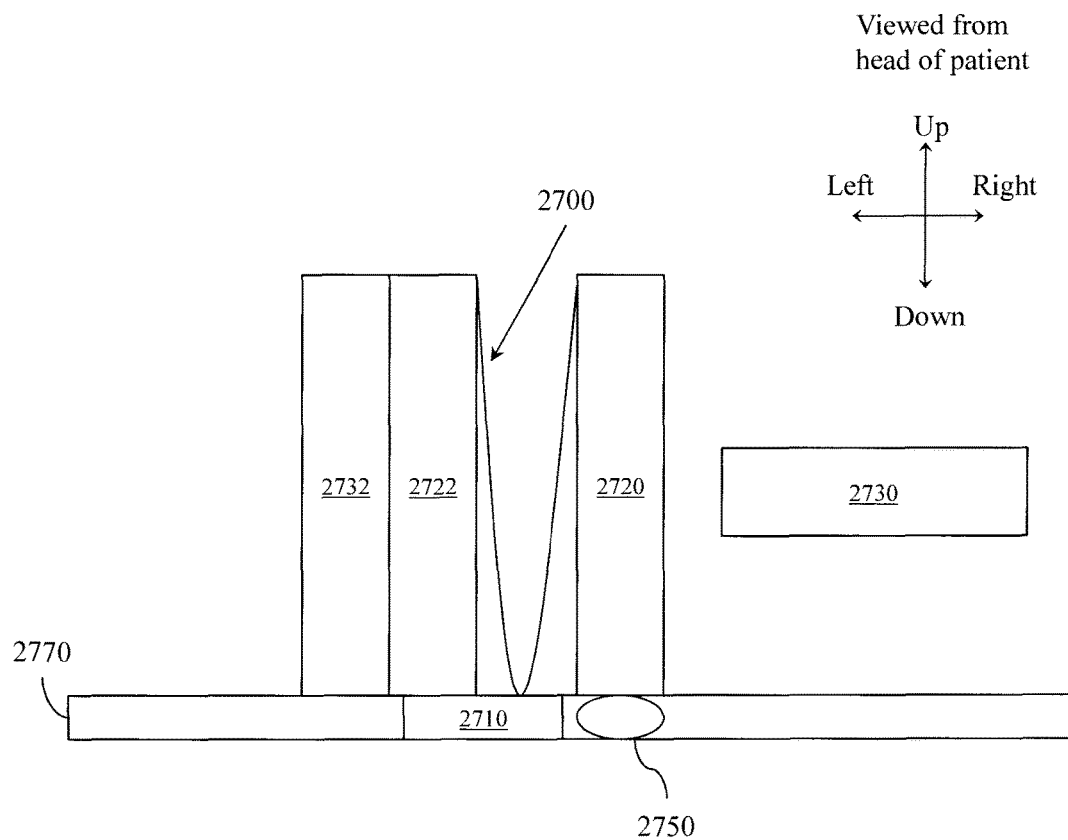
FIG. 23 illustrates a portion of an example reconfigurable MRI-guided surgical apparatus.
Figure 24:
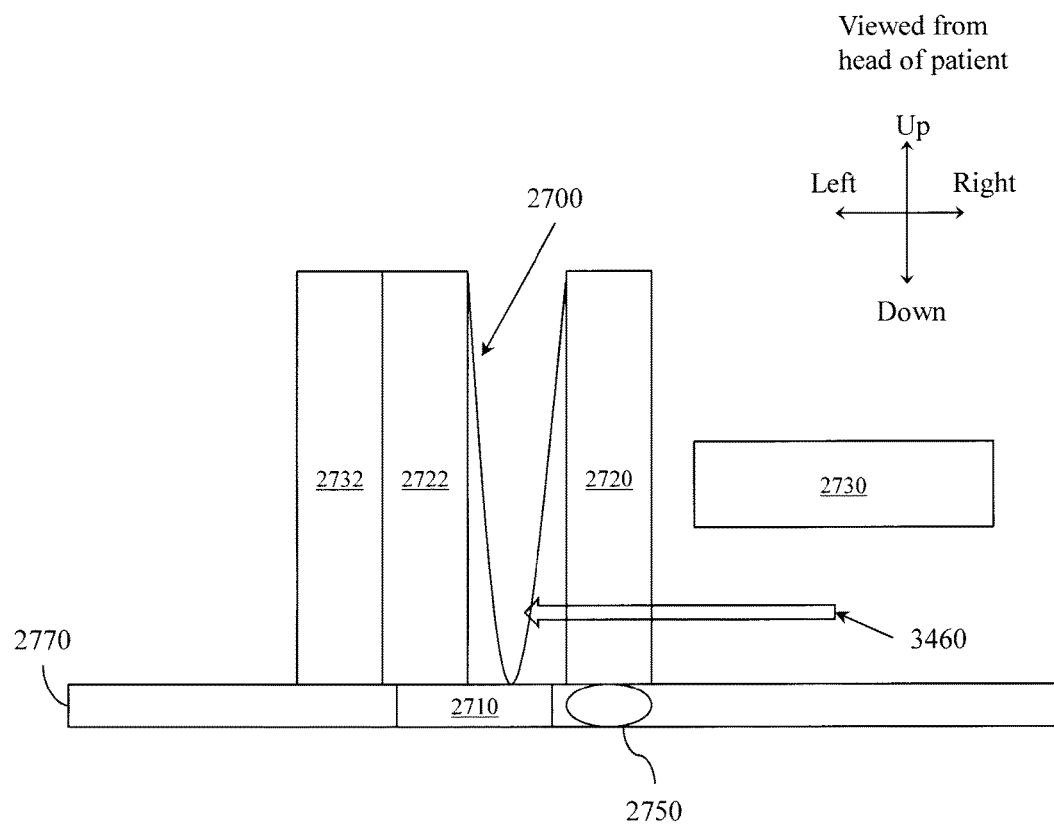
FIG. 24 illustrates a portion of an example reconfigurable MRI-guided surgical apparatus.

FIG. 23 illustrates the side coil 2730 having been moved to facilitate accessing breast 2700 via medical instrument guidance assembly 2720. FIG. 24 illustrates breast 2700 with a needle 3460 inserted via medical instrument guidance assembly 2720. In one embodiment, side coil 2730 may simply be removed to provide access to assembly 2720. In one embodiment, side coil 2730 may have been used to compress breast 2700 and then may have been removed and replaced by assembly 2720.

Figure 25:
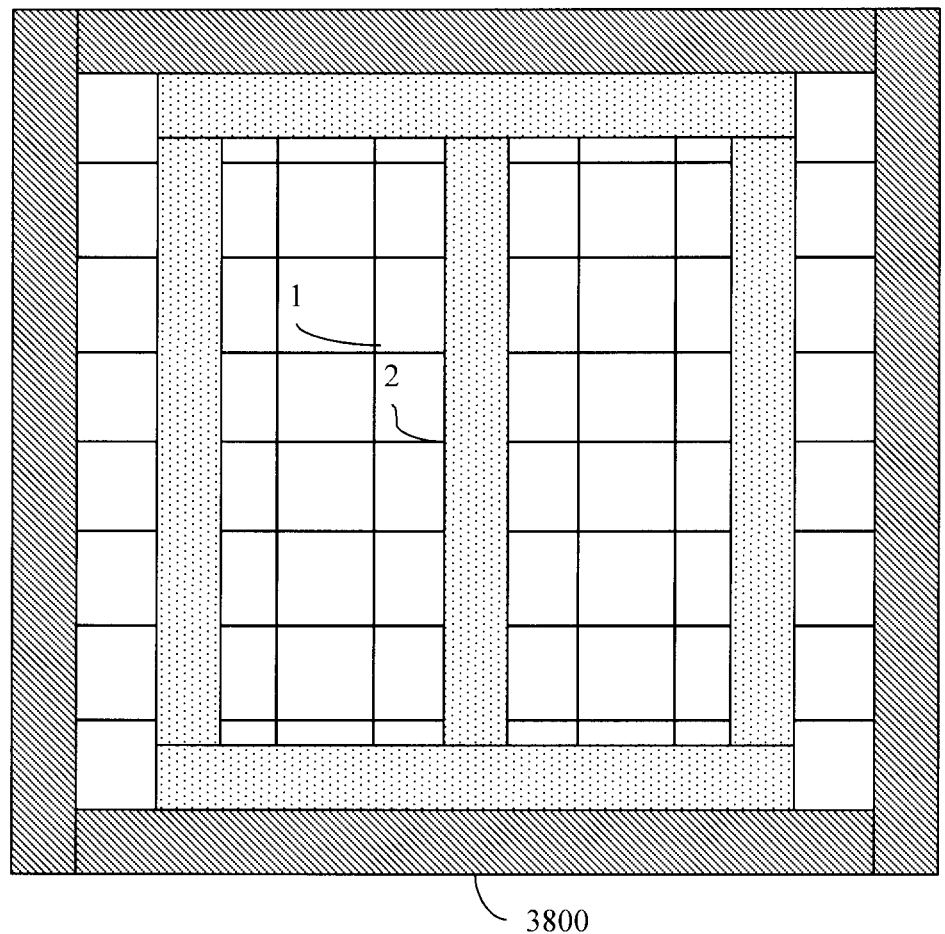
FIG. 25 illustrates a biopsy plate in a frame with a slidable coil.
Figure 25:
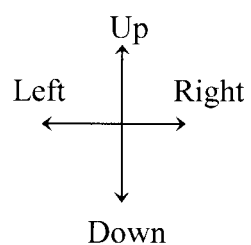

FIG. 25 illustrates a frame 3800 that houses a biopsy plate 1 and a coil 2. Frame 3800, coil 2, and biopsy plate 1 facilitate acquiring an MR image of an object. Frame 3800, coil 2, and biopsy plate 1 also facilitate positioning a needle during an MRI guided procedure. In one embodiment, the needle can be placed without having to move the coil 2. In one embodiment, the coil 2 may have openings that facilitate accessing biopsy plate 1. In one embodiment, both coil 2 and biopsy plate 1 may be housed in the same frame 3800. Coil 2 and biopsy plate 1 may have different sizes. For example, coil 2 may be larger than biopsy plate 1, may be the same size as biopsy plate 1, or may be smaller than biopsy plate 1. Similarly, coil 2 and frame 3800 may have different sizes. For example, coil 2 may be larger than frame 3800, may be the same size as frame 3800, or may be smaller than frame 3800. Even if the coil 2 has openings or is smaller than the frame 3800, portions of coil 2 may block access to portions of biopsy plate 1. Thus, coil 2 may be used for imaging and may then be removed from frame 3800 to provide access to biopsy plate 1.

Figure 26:
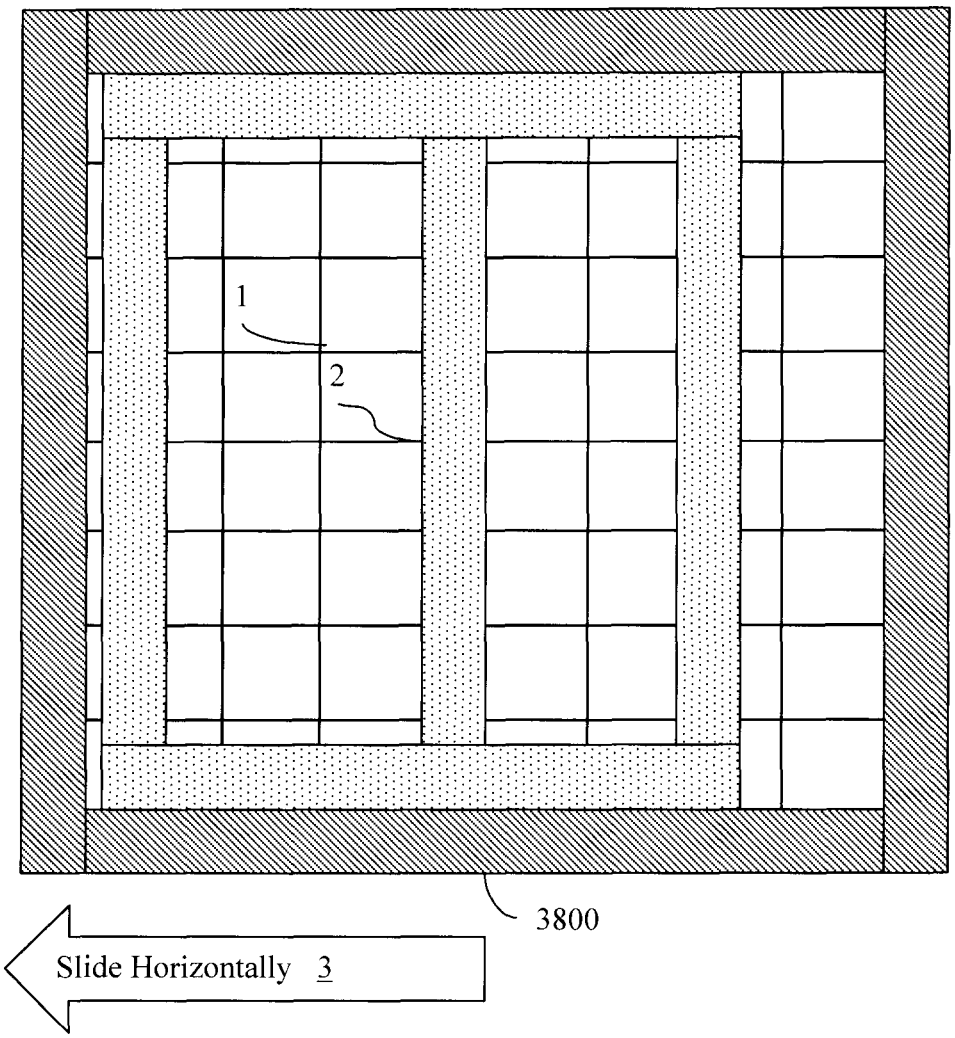
FIG. 26 illustrates a biopsy plate in a frame with a slidable coil.
Figure 26:
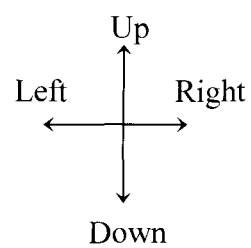

FIG. 26 illustrates frame 3800 with coil 2 after it has been displaced in the horizontal direction indicated by arrow 3. In one embodiment, the coil 2 may be able to be slid left to right in frame 3800. In another embodiment, the coil 2 may be able to be slid up and down in frame 3800. In another embodiment, coil 2 may be able to be rotated in frame 3800. In yet another embodiment, coil 2 may be removable from frame 3800.

More generally, a portion of an inner assembly may include an apparatus that includes a frame or other support configured to hold a biopsy plate and a coil in a position that facilitates acquiring an MR image during an MRI-guided procedure. The coil may allow access to the biopsy plate while the coil is in place. Additionally, the frame or other support may allow the coil to be repositioned yet still remain in a position from which the coil can function to acquire an image during the MRI-guided procedure. The frame or other support may also be configured to allow removal of the coil while leaving the biopsy plate in place.

In one embodiment, an example apparatus for use in a magnetic resonance imaging (MRI) guided medical procedure on a patient's breast includes a support structure configured to support a patient in a face-down prone position. A breast of the patient is positioned in a first free hanging pre-imaging position. The example apparatus also includes an immobilization structure configured to reposition the breast into an immobilized position suitable for MRI and for medical instrument access.

In one example, the immobilization structure includes a biopsy plate or other medical instrument guidance assembly, a pressure plate, and an MRI coil. The MRI coil may be repositioned from a first position associated with the free hanging pre-imaging position to a second position associated with the immobilized position. In this example, a signal to noise ratio (SNR) associated with signal received from the breast through the MRI coil is improved by repositioning the coil from the first position to the second position.

In one embodiment, the coil has an opening sufficient to allow access to the breast through the biopsy plate or other medical instrument guidance assembly through the MRI coil. In one embodiment, the coil is movable from an initial position to a subsequent position so that a portion of the biopsy plate or other medical instrument guidance assembly that is inaccessible while the coil is in the initial position is accessible while the coil is in the subsequent position. An MR image of the breast can be acquired with the coil in either of the initial position or the subsequent position. In one embodiment, the coil is removable from the immobilization structure.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

An "operable connection", or a connection by which entities are "operably connected", is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, software). Logical and/or physical communication channels can be used to create an operable connection.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

What is claimed is:

1. An inner assembly for use with a breast coil in a magnetic resonance imaging (MRI) guided medical procedure on a patient's breast, the inner assembly comprising:
a side coil configured to participate in MRI of the breast, the side coil being configured to be inserted into and removed from the inner assembly, where an MRI of the breast acquired with the side coil in the inner assembly will have a first, higher signal to noise ratio (SNR), and where an MRI of the breast acquired with the side coil removed from the inner assembly will have a second, lower SNR, where the side coil is configured to operate as a receive coil or as a transmit coil;

a medical instrument guidance assembly configured to contact the breast, the medical instrument guidance assembly being configured to be inserted into and removed from the inner assembly;

a brace assembly configured to contact the breast; and a guide configured to movably and lockably position the medical instrument guidance assembly, the side coil, and the brace assembly in both an imaging mode and a procedure mode, the guide being configured to allow insertion and removal of the side coil and the medical instrument guidance assembly, the medical instrument guidance assembly, the side coil, and the brace assembly being movably engaged to the guide, and the guide being configured for positioning the medical instrument guidance assembly on a first side of the breast and for positioning the brace assembly on a second, opposing side of the breast to facilitate applying to the breast a force sufficient to hold the breast against the medical instrument guidance assembly in a fixed spatial relationship having a desired tolerance during the MRI-guided medical procedure.

2. The inner assembly of claim 1, the guide being configured to control and allow movement of the side coil from a first position to a second position, where a signal received from the breast by the side coil in the first position during the MRI-guided surgical procedure yields a first signal to noise ratio (SNR), and where a signal received from the breast by the side coil in the second position during the MRI-guided surgical procedure yields a second, higher SNR.

3. The inner assembly of claim 1, where the medical instrument guidance assembly is a biopsy plate.

4. The inner assembly of claim 1, where the medical instrument guidance assembly is a pillar and post assembly, and where the medical instrument guidance assembly is computer controlled.

5. The inner assembly of claim 1, where the medical instrument guidance assembly is a pillar and post assembly configured with pressure rails.

6. The inner assembly of claim 1, where the medical instrument guidance assembly includes a robotic assembly, and where the medical instrument guidance assembly is computer controlled.

7. The inner assembly of claim 1, where the medical instrument guidance assembly includes a robotic assembly configured with pressure rails, and where the medical instrument guidance assembly is computer controlled.

8. An inner assembly for use with a breast coil in a magnetic resonance imaging (MRI) guided medical procedure on a patient's breast, the inner assembly comprising:
a side coil configured to participate in MRI of the breast, the side coil being configured to be inserted into and removed from the inner assembly, where the side coil is configured to operate as a receive coil or as a transmit coil;
a medical instrument guidance assembly configured to contact the breast, the medical instrument guidance assembly being configured to be inserted into and removed from the inner assembly; and
a guide configured to facilitate repositioning the medical instrument guidance assembly and the side coil to support an imaging mode and a procedure mode, where an MRI image acquired in the imaging mode with the side coil in place in the inner assembly will have a first, higher signal to noise ratio (SNR) and where an MRI image acquired in the procedure mode with the side coil removed from the inner assembly will have a second, lower SNR,
the medical instrument guidance assembly and the side coil being movably engaged to the guide,
the medical instrument guidance assembly being positionable to facilitate applying to the breast a force sufficient to hold the breast in a fixed spatial relationship having a desired tolerance during the MRI-guided medical procedure,
the guide being configured to control and allow insertion and removal of the side coil.

9. The inner assembly of claim 8, where the medical instrument guidance assembly is a biopsy plate.

10. The inner assembly of claim 8, where the medical instrument guidance assembly is a pillar and post assembly, and where the medical instrument guidance assembly is computer controlled.

11. The inner assembly of claim 8, where the medical instrument guidance assembly is a pillar and post assembly configured with pressure rails.

12. The inner assembly of claim 8, where the medical instrument guidance assembly includes a robotic assembly, and where the medical instrument guidance assembly is computer controlled.

13. The inner assembly of claim 8, where the medical instrument guidance assembly includes a robotic assembly configured with pressure rails, and where the medical instrument guidance assembly is computer controlled.

14. An inner assembly for use with a breast coil in a magnetic resonance imaging (MRI) guided medical procedure on a patient's breast, the inner assembly comprising:
a side coil configured to participate in MRI of the breast, the side coil being configured to be inserted into and removed from the inner assembly, where the side coil is configured to operate as a receive coil or as a transmit coil;
a medical instrument guidance assembly configured to be inserted into and removed from the inner assembly; and
a guide configured to facilitate repositioning, inserting, or removing the medical instrument guidance assembly and the side coil to support an imaging mode and a procedure mode,
where the guide facilitates positioning the breast in a fixed spatial relationship having a desired tolerance during the MRI-guided medical procedure.

15. The inner assembly of claim 14, where the medical instrument guidance assembly is a biopsy plate.

16. The inner assembly of claim 14, where the medical instrument guidance assembly is a pillar and post assembly, and where the medical instrument guidance assembly is computer controlled.

17. The inner assembly of claim 14, where the medical instrument guidance assembly is a pillar and post assembly configured with pressure rails.

18. The inner assembly of claim 14, where the medical instrument guidance assembly includes a robotic assembly and where the medical instrument guidance assembly is computer controlled.

19. The inner assembly of claim 14, where the medical instrument guidance assembly includes a robotic assembly configured with pressure rails.

* * * * *